United States Patent
Kassab

(10) Patent No.: US 10,217,220 B2
(45) Date of Patent: Feb. 26, 2019

(54) METHODS FOR THE DETERMINATION OF TRANSIT TIME IN CIRCULATORY SYSTEMS AND APPLICATIONS OF THE SAME

(71) Applicants: DTherapeutics, LLC, San Diego, CA (US); Ghassan S. Kassab, La Jolla, CA (US)

(72) Inventor: Ghassan S. Kassab, La Jolla, CA (US)

(73) Assignee: DTherapeutics, LLC, San Diego, CA (US)

( * ) Notice: Subject to any disclaimer, the term of this patent is extended or adjusted under 35 U.S.C. 154(b) by 108 days.

(21) Appl. No.: 15/168,807

(22) Filed: May 31, 2016

(65) Prior Publication Data

US 2016/0350920 A1 Dec. 1, 2016

Related U.S. Application Data

(63) Continuation-in-part of application No. 13/106,027, filed on May 12, 2011, now Pat. No. 9,591,994,
(Continued)

(51) Int. Cl.
| | |
|---|---|
| *G06T 7/00* | (2017.01) |
| *G06T 7/60* | (2017.01) |
| *A61B 5/02* | (2006.01) |
| *A61B 6/00* | (2006.01) |
| *A61B 5/026* | (2006.01) |
| *A61B 5/107* | (2006.01) |

(Continued)

(52) U.S. Cl.
CPC ............ *G06T 7/0016* (2013.01); *A61B 5/026* (2013.01); *A61B 5/02007* (2013.01); *A61B 5/1076* (2013.01); *A61B 6/507* (2013.01); *G06T 7/62* (2017.01); *A61B 5/0013* (2013.01); *A61B 5/055* (2013.01); *A61B 5/7275* (2013.01); *G06T 2207/30048* (2013.01); *G06T 2207/30104* (2013.01)

(58) Field of Classification Search
CPC ..... A61B 5/02007; A61B 5/026; A61B 5/055; A61B 10/02; A61B 2034/105; A61B 2034/108; A61B 34/10; A61B 5/0013; A61B 5/1076; A61B 5/4839; A61B 5/7275; A61B 6/504; A61B 6/507; G06F 19/3437; G06F 19/3456; G06T 2207/30048; G06T 2207/30104; G06T 7/0016; G06T 7/62
USPC .......... 702/19, 156, 157, 158; 600/420, 431, 600/454, 481, 508, 538; 703/11
See application file for complete search history.

(56) References Cited

U.S. PATENT DOCUMENTS 5,150,292 A * 9/1992 Hoffmann .............. A61B 6/481
250/303

* cited by examiner

*Primary Examiner* — John H Le
(74) *Attorney, Agent, or Firm* — Reichel Stohry LLP; Mark C. Reichel; Natalie J. Dean

(57) ABSTRACT

Methods for the determination of transit time in circulatory systems and applications of the same. In at least one embodiment, the method includes the steps of obtaining a biological tree image showing a vasculature of at least part of a mammalian biological tree including at least a vessel segment, determining a transit time in the vessel segment, determining a blood volume in the vessel segment, determining a blood volume in a first vascular tree comprising the vessel segment, and calculating a transit time in the first vascular tree based upon the transit time through the vessel segment, the blood volume in the vessel segment, and the blood volume in the first vascular tree.

16 Claims, 34 Drawing Sheets

Related U.S. Application Data which is a continuation-in-part of application No. 12/864,016, filed as application No. PCT/US2008/072925 on Aug. 12, 2008, now Pat. No. 8,670,943, which is a continuation-in-part of application No. PCT/US2008/000762, filed on Jan. 22, 2008, application No. 15/168,807, filed on May 31, 2016, which is a continuation-in-part of application No. 14/205,035, filed on Mar. 11, 2014, now Pat. No. 9,775,576, which is a continuation of application No. 12/864,016, filed on Jul. 22, 2010, now Pat. No. 8,670,943.

(60) Provisional application No. 62/167,557, filed on May 28, 2015, provisional application No. 60/881,833, filed on Jan. 23, 2007.

(51) Int. Cl.
*G06T 7/62* (2017.01)
*A61B 5/00* (2006.01)
*A61B 5/055* (2006.01)

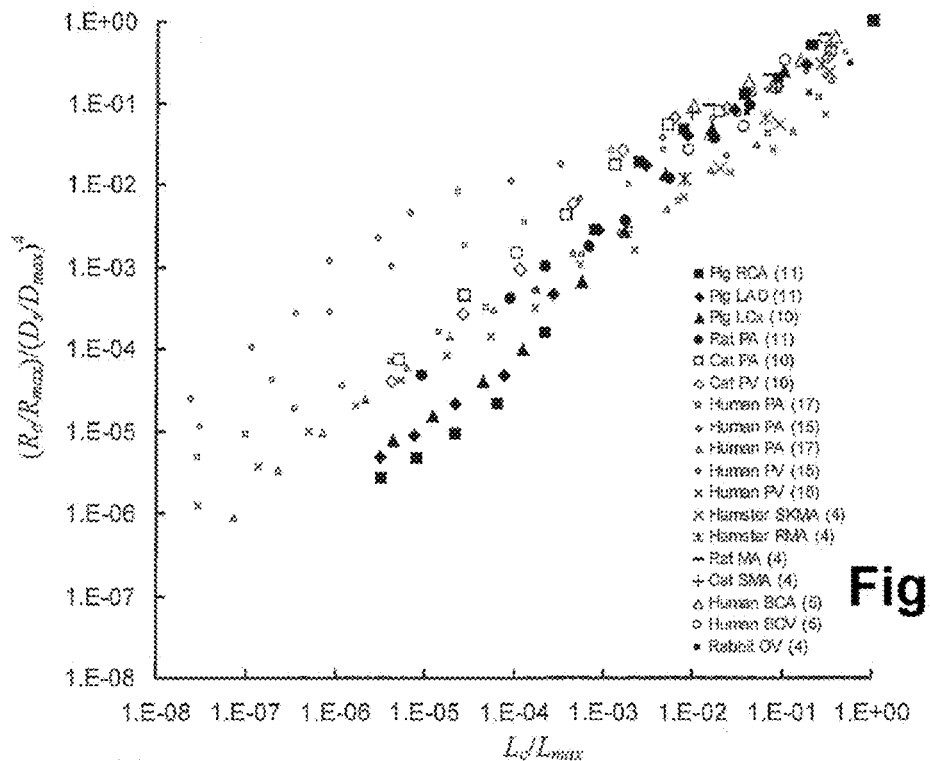
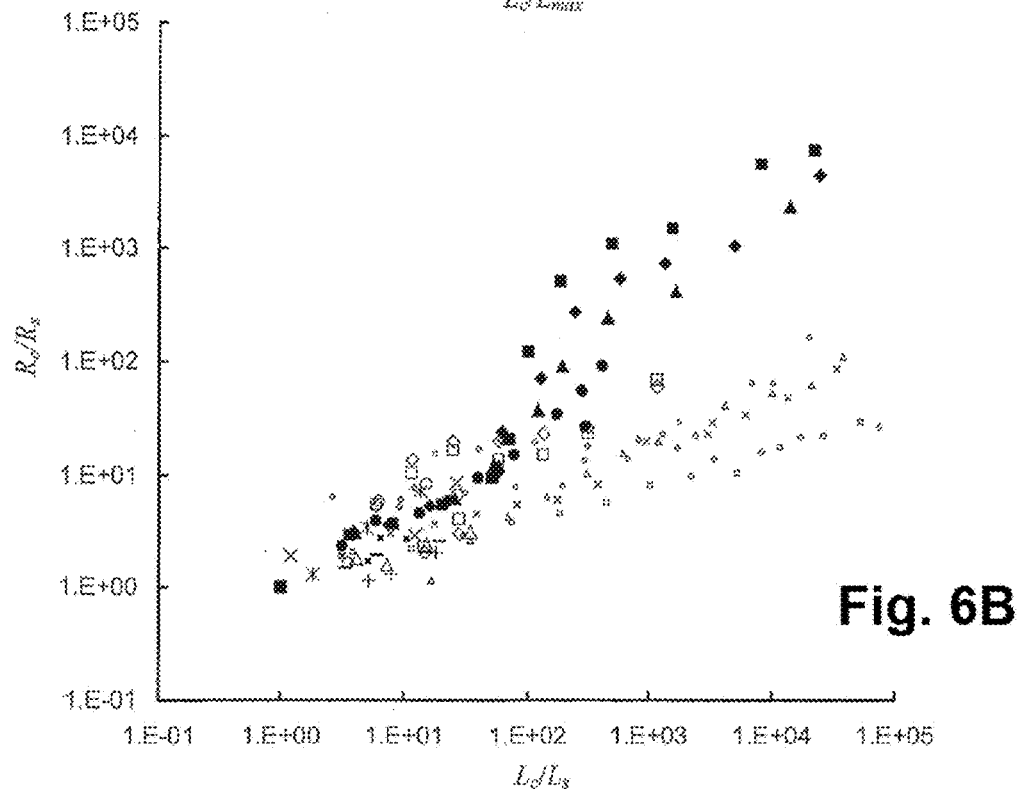

| Species | Vessel (N) | $A_1$ | $R^2$ | $(K_s/K_c)_{ML}$ | $R^2$ |
|---|---|---|---|---|---|
| Pig | RCA (11) | 1.06 | 0.93 | 2.38 | 0.88 |
| Pig | LAD (11) | 1.02 | 0.99 | 5.32 | 0.97 |
| Pig | LCx (10) | 1.01 | 0.98 | 5.79 | 0.99 |
| Rat | PA (11) | 1.07 | 0.90 | 5.03 | 0.86 |
| Cat | PA (10) | 1.03 | 0.98 | 24.3 | 0.90 |
| Cat | PV (10) | 1.02 | 0.99 | 14.1 | 0.85 |
| Human | PA (17) | 0.97 | 0.98 | 2002 | 0.85 |
| Human | PA (15) | 0.98 | 0.98 | 1956 | 0.91 |
| Human | PA (17) | 0.95 | 0.97 | 445 | 0.80 |
| Human | PV (15) | 0.97 | 0.98 | 726 | 0.96 |
| Human | PV (15) | 0.94 | 0.95 | 96.3 | 0.95 |
| Hamster | SKMA (4) | 0.97 | 0.98 | 1.16 | 0.92 |
| Hamster | RMA (4) | 1.00 | 1.00 | 1.76 | 0.98 |
| Rat | MA (4) | 1.11 | 0.83 | 4.99 | 0.55 |
| Cat | SMA (4) | 1.04 | 0.96 | 6.66 | 0.61 |
| Human | BCA (5) | 1.11 | 0.88 | 7.40 | 0.60 |
| Human | BCV (5) | 1.10 | 0.86 | 2.35 | 0.54 |
| Rabbit | OV (4) | 0.88 | 0.90 | 3.11 | 0.68 |

Fig. 7A

| Entire Trees | Least-Square Fit | | Marquardt-Levenberg Method | | |
|---|---|---|---|---|---|
| | $B$ | $R^2$ | $A$ | SE | $R^2$ |
| Pig LAD | 1.07 | 1 | 1.02 | 0.006 | 0.998 |
| Pig LCx0 | 1.08 | 1 | 0.99 | 0.008 | 0.997 |
| Pig RCA | 1.08 | 1 | 0.99 | 0.014 | 0.989 |
| Epicardial Trees | Least-Square Fit | | Marquardt-Levenberg Method | | |
| | $B$ | $R^2$ | $A$ | SE | $R^2$ |
| Pig LAD | 1.07 | 0.995 | 0.95 | 0.008 | 0.996 |
| Pig LCx | 1.03 | 0.994 | 0.97 | 0.013 | 0.994 |
| Pig RCA | 1.08 | 0.990 | 1.02 | 0.019 | 0.986 |

Fig. 9

|  | Least-Square Fit | | Marquardt-Levenberg Method | | |
| --- | --- | --- | --- | --- | --- |
| Species (N) | $B$ | $R^2$ | $A$ | SE | $R^2$ |
| Pig RCA (11) | 1.09 | 0.999 | 1 | 0.003 | 1 |
| Pig LAD (11) | 1.10 | 0.999 | 1 | 0 | 1 |
| Pig LCx (10) | 1.13 | 0.999 | 1 | 0.001 | 1 |
| Rat PA (11) | 1.06 | 0.999 | 0.99 | 0.017 | 0.997 |
| Cat PA (10) | 1.11 | 0.996 | 1.01 | 0.013 | 0.999 |
| Cat PV (10) | 1.09 | 1 | 0.99 | 0.018 | 0.997 |
| Human PA (17) | 0.88 | 1 | 1 | 0.004 | 1 |
| Human PA (15) | 0.95 | 0.998 | 1.02 | 0.025 | 0.991 |
| Human PA (17) | 0.92 | 1 | 0.997 | 0.006 | 0.999 |
| Human PV (15) | 1.05 | 0.995 | 1.02 | 0.019 | 0.996 |
| Human PV (15) | 0.94 | 1 | 1.01 | 0.014 | 0.997 |
| Hamster SKMA (4) | 1.02 | 0.995 | 1.01 | 0.031 | 0.997 |
| Rat MA (4) | 1 | 1 | 1 | 0.007 | 1 |
| Rabbit OV (4) | 0.98 | 0.994 | 0.96 | 0.073 | 0.981 |
| Human BCA (5) | 0.98 | 1 | 1.01 | 0.015 | 0.999 |
| Human BCV (4) | 1.02 | 1 | 1 | 0.004 | 1 |
| Hamster RMA (4) | 1.03 | 0.977 | 1 | 0.014 | 0.999 |
| Cat SMA (4) | 0.95 | 1 | 1 | 0.012 | 1 |

Fig. 10

| Species | Diameter-Length | | | Volume-Length | | | Flow-Diameter | | | Volume-Diameter | | |
|---|---|---|---|---|---|---|---|---|---|---|---|---|
| | A | SE | $R^2$ | A | SE | $R^2$ | A | SE | $R^2$ | A | SE | $R^2$ |
| Pig RCA | 1.01 | 0.010 | 0.999 | 1 | 0.002 | 1 | 1 | 0.007 | 1 | 1 | 0.007 | 0.999 |
| Pig LAD | 1.02 | 0.019 | 0.996 | 1 | 0.003 | 1 | 0.99 | 0.017 | 0.997 | 1 | 0.01 | 0.999 |
| Pig LCx | 1 | 0.007 | 1 | 1 | 0.001 | 1 | 1 | 0.001 | 1 | 1 | 0.001 | 1 |
| Rat PA | 1.02 | 0.021 | 0.995 | 0.99 | 0.014 | 0.998 | 0.98 | 0.021 | 0.995 | 0.98 | 0.032 | 0.99 |
| Cat PA | 1 | 0.014 | 0.998 | 1.01 | 0.011 | 0.999 | 1.01 | 0.006 | 1 | 1.01 | 0.017 | 0.998 |
| Cat PV | 0.99 | 0.017 | 0.997 | 0.99 | 0.020 | 0.996 | 1.01 | 0.012 | 0.999 | 0.99 | 0.01 | 0.999 |
| Human PA | 0.92 | 0.037 | 0.977 | 1 | 0.006 | 0.999 | 1.02 | 0.034 | 0.982 | 1.01 | 0.022 | 0.993 |
| Human PA | 0.97 | 0.025 | 0.991 | 1.01 | 0.020 | 0.995 | 1.02 | 0.025 | 0.992 | 1.02 | 0.041 | 0.977 |
| Human PA | 0.90 | 0.041 | 0.973 | 0.99 | 0.014 | 0.997 | 1.03 | 0.041 | 0.974 | 1.01 | 0.021 | 0.993 |
| Human PV | 0.96 | 0.016 | 0.996 | 1.02 | 0.013 | 0.998 | 1.04 | 0.029 | 0.990 | 1.04 | 0.041 | 0.979 |
| Human PV | 0.88 | 0.054 | 0.955 | 1 | 0.001 | 1 | 1.02 | 0.053 | 0.963 | 1.01 | 0.041 | 0.976 |
| Hamster SKMA | 0.96 | 0.096 | 0.942 | 1 | 0.015 | 0.999 | 1.03 | 0.087 | 0.974 | 1.02 | 0.079 | 0.98 |
| Rat MA | 1.13 | 0.203 | 0.592 | 1.01 | 0.034 | 0.996 | 0.89 | 0.156 | 0.914 | 0.92 | 0.132 | 0.944 |
| Rabbit OV | 1.02 | 0.107 | 0.849 | 0.95 | 0.081 | 0.977 | 1.06 | 0.107 | 0.954 | 0.97 | 0.062 | 0.987 |
| Human BCA | 1.14 | 0.190 | 0.447 | 1.02 | 0.038 | 0.994 | 0.88 | 0.133 | 0.912 | 0.92 | 0.099 | 0.955 |
| Human BCV | 1.06 | 0.068 | 0.964 | 1 | 0.009 | 1 | 0.96 | 0.061 | 0.983 | 0.97 | 0.056 | 0.987 |
| Hamster RMA | 1.03 | 0.078 | 0.965 | 1 | 0.017 | 0.999 | 1.01 | 0.029 | 0.997 | 1 | 0.006 | 1 |
| Cat SMA | 1.11 | 0.193 | 0.633 | 1.01 | 0.034 | 0.996 | 0.92 | 0.133 | 0.938 | 0.95 | 0.103 | 0.966 |

Fig. 11

$$\left(\frac{D_s}{D_{max}}\right)^{\frac{2}{3}}\left(\frac{L_c}{L_{max}}\right)$$

Fig. 16

Bifurcation diameter models and the corresponding physical mechanisms

| Bifurcation Diameter Models | Relationship | Physical Mechanisms |
|---|---|---|
| HK | $D_m^{\frac{7}{3}} = D_l^{\frac{7}{3}} + D_s^{\frac{7}{3}}$ | Minimum Energy |
| Finet | $D_m = 0.678 \times (D_l + D_s)$ | "Fractal"-type relation |
| Murray | $D_m^3 = D_l^3 + D_s^3$ | Minimum Energy & WSS ~ Constant |
| Area-Preservation | $D_m^2 = D_l^2 + D_s^2$ | Velocity ~ Constant |

$D_m$, $D_l$, and $D_s$ are diameters of mother, larger and smaller daughter vessels, respectively.

(A) Y-type bifurcation (B) T-type bifurcation

Fig. 19

$\dfrac{D_m}{D_l + D_s}$ in Y and T bifurcations determined by the HK, Murray, and area-preservation models

| $D_s/D_l$ | $\dfrac{D_m}{D_l + D_s}$, Y-type bifurcation | | | $D_s/D_l$ | $\dfrac{D_m}{D_l + D_s}$, T-type bifurcation | | |
|---|---|---|---|---|---|---|---|
| | HK | Murray | Area-preservation | | HK | Murray | Area-preservation |
| 0.75 | 0.682 | 0.643 | 0.714 | 0.25 | 0.813 | 0.804 | 0.825 |
| 0.8 | 0.678 | 0.638 | 0.711 | 0.2 | 0.842 | 0.836 | 0.850 |
| 0.85 | 0.676 | 0.634 | 0.709 | 0.15 | 0.874 | 0.871 | 0.879 |
| 0.9 | 0.674 | 0.632 | 0.708 | 0.1 | 0.911 | 0.909 | 0.914 |
| 0.95 | 0.673 | 0.630 | 0.707 | 0.05 | 0.953 | 0.952 | 0.954 |
| 1 | 0.673 | 0.630 | 0.707 | 0 | 1 | 1 | 1 |
| Mean± SE | 0.676± 0.001 | 0.634± 0.002 | 0.710± 0.001 | Mean± SE | 0.9± 0.028 | 0.895± 0.03 | 0.903± 0.027 |

The daughter diameter ratio ($D_s/D_l$) is assumed to have values of 0.75 to one for Y-type bifurcation and 0.75 to 0 for T-type bifurcation. Only the HK model shows good agreement with Finet model in Y-type bifurcation (i.e., 0.676 vs. 0.678).

Fig. 20

Relative errors between bifurcation diameter models and measurements of quantitative coronary bifurcation angiography in Table 1 of Ref. 3.

| Mother Vessel | %Error$_{HK}$ | %Error$_{Finet}$ | %Error$_{Murray}$ | %Error$_{AP}$ | n |
|---|---|---|---|---|---|
| $4.5 \leq D_m$ | -1.33 | -0.36 | -18.73 | 8.86 | 21 |
| $4 \leq D_m < 4.5$ | -2.03 | -0.58 | -19.57 | 8.25 | 24 |
| $3.5 \leq D_m < 4$ | 1.02 | 0.48 | -16.02 | 10.99 | 18 |
| $3 \leq D_m < 3.5$ | -5.6 | -2.59 | -22.87 | 4.60 | 43 |
| $2.5 \leq D_m < 3$ | 8.53 | 3.65 | -7.96 | 18.04 | 33 |
| $D_m \leq 2.5$ | 8.77 | 4.08 | -8.14 | 18.44 | 35 |
| For all | 0.57 | 0.39 | -16.62 | 10.62 | 173 |

$\%Error_{HK} = \frac{\left(D_l^{2\frac{1}{3}} * D_s^{2\frac{3}{8}} - D_m^{2\frac{1}{3}}\right)}{D_m^{2\frac{1}{3}}} \times 100\%$ for HK model; $\%Error_{Finet} = \frac{[(D_l + D_s) \cdot 0.678 - D_m]}{D_m} \times 100\%$ for Finet model; $\%Error_{Murray} = \frac{\left(D_l^3 + D_s^3 - D_m^3\right)}{D_m^3} \times 100\%$ for Murray; and $\%Error_{AP} = \frac{\left(D_l^2 + D_s^2 - D_m^2\right)}{D_m^2} \times 100\%$ for area-preservation models. "n" represents number of measurements.

Fig. 21

Relative errors between bifurcation diameter models and measurements in the LAD tree of a porcine heart with mother diameters ≥ 0.5 mm obtained from casts of Ref. 5.

| $D_s/D_l$ | % Error$_{HK}$ | % Error$_{Finet}$ | % Error$_{Murray}$ | % Error$_{AP}$ | n |
|---|---|---|---|---|---|
| $D_s/D_l \leq 0.1$ | 0.54±2.46 | -27.31±0.78* | 0.95±3.28 | 0.66±2.09 | 53 |
| $0.1 < D_s/D_l \leq 0.2$ | -4.67±1.34 | -24.45±0.48* | -6.75±1.68 | -2.99±1.17 | 92 |
| $0.2 < D_s/D_l \leq 0.3$ | -0.50±1.85 | -16.92±0.68* | -3.64±2.30 | 2.26±1.63 | 76 |
| $0.3 < D_s/D_l \leq 0.4$ | -5.95±3.55 | -14.93±1.63* | -12.27±4 | -1.26±3.31 | 42 |
| $0.4 < D_s/D_l \leq 0.5$ | -0.74±3.62 | -8.12±1.54 | -9.77±4.11 | 5.44±3.34 | 33 |
| $0.5 < D_s/D_l \leq 0.6$ | 0.52±4.06 | -4.65±1.72 | -11.11±4.57* | 7.98±3.77 | 21 |
| $0.6 < D_s/D_l \leq 0.7$ | 5.21±3.38 | -0.42±1.41 | -8.30±3.74* | 13.47±3.15 | 35 |
| $0.7 < D_s/D_l \leq 0.8$ | 4.10±5.03 | 0.74±2.17 | -11.45±5.40* | 13.31±4.74 | 17 |
| $0.8 < D_s/D_l \leq 0.9$ | 3.69±4.10 | 0.92±1.67 | -12.27±4.54 | 13.11±3.81 | 15 |
| $0.9 < D_s/D_l$ | -5.97±6.18 | -2.94±3.09 | -23.12±6.19* | 4.20±6.03 | 17 |
| Mean ± SE | -0.47±1.26 | -9.81±3.31* | -9.91±2.02* | 5.55±1.92* | 401 |

$\%Error_{HK} = \frac{\left(D_l^{2\frac{1}{3}} + D_s^{2\frac{1}{3}} \cdot D_m^{2\frac{1}{3}}\right)}{D_m^{2\frac{1}{3}}} \times 100\%$ for HK model; $\%Error_{Finet} = \frac{[(D_l + D_s) \cdot 0.678 - D_m]}{D_m} \times 100\%$ for Finet model; $\%Error_{Murray} = \frac{(D_l^3 + D_s^3 \cdot D_m^3)}{D_m^3} \times 100\%$ for Murray; and $\%Error_{AP} = \frac{(D_l^2 + D_s^2 \cdot D_m^2)}{D_m^2} \times 100\%$ for area-preservation models. Symbol * represents the significant difference (P < 0.05) between HK model and the corresponding model (i.e., Finet, Murray, and area-preservation models). "n" represents number of measurements.

Fig. 23

The optimal diameter can be determined at a bifurcation when other two diameters are input.

For examples: Input values for $D_m$ and $D_l$:

$D_m$: [ 5 ]   $D_l$: [ 4 ]   $D_s$: [      ]   [Calculate]

After clicking button "Calculate", $D_s$ will be determined as follows:

$D_m$: [ 5 ]   $D_l$: [ 4 ]   $D_s$: [ 3.397 ]

Alternatively, input values for $D_m$ and $D_s$:

$D_m$: [ 4 ]   $D_l$: [      ]   $D_s$: [ 2 ]   [Calculate]

After clicking button "Calculate", $D_l$ will be determined as follows:

$D_m$: [ 4 ]   $D_l$: [ 3.638 ]   $D_s$: [ 2 ]

Alternatively, input values for $D_l$ and $D_s$:

$D_m$: [      ]   $D_l$: [ 3.5 ]   $D_s$: [ 2.5 ]   [Calculate]

After clicking button "Calculate", $D_m$ will be determined as follows:

$D_m$: [ 4.112 ]   $D_l$: [ 3.5 ]   $D_s$: [ 2.5 ]

METHODS FOR THE DETERMINATION OF TRANSIT TIME IN CIRCULATORY SYSTEMS AND APPLICATIONS OF THE SAME

PRIORITY

This application a) is related to, and claims the priority benefit of, U.S. Provisional Patent Application Ser. No. 62/167,557, filed May 28, 2015, b) is related to, claims the priority benefit of, and is a U.S. continuation-in-part patent application of, U.S. patent application Ser. No. 13/106,027, filed May 12, 2011, which is related to, claims the priority benefit of, and is a U.S. continuation-in-part patent application of, U.S. patent application Ser. No. 12/864,016, filed Jul. 22, 2010 and issued as U.S. Pat. No. 8,670,943 on Mar. 11, 2014, which is related to, claims the priority benefit of, and is a U.S. Section 371 national stage patent application of, International Patent Application Serial No. PCT/US2008/072925, filed Aug. 12, 2008, which is related to, claims the priority benefit of, and is an international continuation-in-part application of, International Patent Application Serial No. PCT/US2008/000762, filed Jan. 22, 2008, which is related to, and claims the priority benefit of, U.S. Provisional Patent Application Ser. No. 60/881,833, filed Jan. 23, 2007, and c) is related to, claims the priority benefit of, and is a U.S. continuation-in-part patent application of, U.S. patent application Ser. No. 14/205,035, filed Mar. 11, 2014, which is related to, claims the priority benefit of, and is a U.S. continuation patent application of, U.S. patent application Ser. No. 12/864,016, filed Jul. 22, 2010 and issued as U.S. Pat. No. 8,670,943 on Mar. 11, 2014, which is related to, claims the priority benefit of, and is a U.S. Section 371 national stage patent application of, International Patent Application Serial No. PCT/US2008/072925, filed Aug. 12, 2008, which is related to, claims the priority benefit of, and is an international continuation-in-part application of, International Patent Application Serial No. PCT/US2008/000762, filed Jan. 22, 2008, which is related to, and claims the priority benefit of, U.S. Provisional Patent Application Ser. No. 60/881,833, filed Jan. 23, 2007. The contents of each of the foregoing applications and patent are hereby incorporated by reference in their entireties into this disclosure.

BACKGROUND

The major role of vascular networks in the circulatory system is to transport blood, oxygen, nutrients, hormones, and cellular waste to and from various organs to maintain biological homeostasis. Accordingly, data points related to the circulation of blood flow through the vasculature are important physiological parameters that dictate biological transport phenomena and often have critical implications for vascular disease and medical diagnosis.

A study of the circulation requires an understanding of not only hemodynamics (blood flow), but also the vasculature's morphological (e.g., diameter, length, volume, etc.) and topological (e.g., connectivity patterns) information, and any potential structure-function relations thereof. Functionally, the vasculature structure serves metabolism where there is an intimate structure-function relation. Indeed, vascular patterns have been used as a basis to elucidate the origin of allometric scaling laws (e.g., the scaling law of metabolism, which can be used to predict structural and functional properties of vertebrate cardiovascular and respiratory systems based on principles of maximizing metabolic capacity and preserving energy dissipation) and various intraspecific scaling laws (e.g., volume-diameter, flow-length, and length-volume relationships and the scaling law of flow resistance).

The mean transit time (MTT), which is the time required to transport blood within a vascular network, plays a vital role in the physiological function of a circulatory system. The vascular network has structure heterogeneity and complexity with respect to the spatial arrangement of vessels, as well as the ability to adapt its anatomy in response to hemodynamic and metabolic stimuli. Accordingly, development of structure-function relationships that relate MTT to vascular morphology are fundamental to understanding the interplay between vascular form and function and, thus, provide a better rationale for clinical diagnostics and therapies. Because this has not yet been achieved, conventional measurement of MTT relies on quantification of blood volume and flow rate, both of which are challenging to accurately determine—particularly in small vessels. Especially considering that MTT is such a seminal physiological parameter with respect to biological transport, it would be beneficial to provide a framework for an accurate and non-invasive way to determine MTT in various species and organs throughout the vasculature.

BRIEF SUMMARY

Exemplary methods of the present disclosure include methods for accurately and noninvasively determining mean transit time in a vascular tree. In at least one embodiment, the method comprises the steps of: obtaining a biological tree image showing a vasculature of at least part of a mammalian biological tree comprising at least a vessel segment; determining a transit time in the vessel segment; determining a blood volume in the vessel segment; determining a blood volume in a first vascular tree comprising the vessel segment; and calculating a transit time in the first vascular tree based upon the transit time through the vessel segment, the blood volume in the vessel segment, and the blood volume in the first vascular tree. In at least one exemplary embodiment of the present method, the transit time in the first vascular tree is calculated without measuring blood flow rates. Additionally or alternatively, the step of obtaining a biological tree image may be performed using a non-invasive imaging technique.

Optionally, the method may further comprise the step of calculating a constant based on a length of the first vascular tree, the blood volume of the first vascular tree, and the calculated transit time in the first vascular tree. Still further, in at least one embodiment, the method may additionally comprise the steps of determining a length and a blood volume of a second vascular tree; and calculating a transit time in the second vascular tree based upon the use of the calculated constant.

In at least one embodiment, the first vascular tree comprises the vasculature of an organ; however, it will be understood that the first vascular tree may comprise any vascular tree within a mammalian body.

In yet another embodiment, a first ratio of the transit time in the vessel segment and the transit time in the first vascular tree and a second ratio of the blood volume in the vessel segment and the blood volume in the first vascular tree may have a linear relationship. In at least one exemplary embodiment, comparing the first ratio with the second ratio may result in a proportionality constant that is equal to about 1.

Additionally exemplary embodiments of the present disclosure include methods for optimizing the dosage of a pharmaceutical compound comprising at least one active ingredient. In at least one exemplary embodiment thereof, the method comprises the steps of: obtaining a biological tree image from a mammalian body showing a vasculature of at least part of a biological tree comprising at least a vessel segment; determining a transit time in the vessel segment; determining a blood volume in the vessel segment; determining a blood volume in a first vascular tree comprising the vessel segment; calculating a transit time in the first vascular tree based upon the transit time through the vessel segment, the blood volume in the vessel segment, and the blood volume in the first vascular tree; and modifying a composition of a pharmaceutical compound comprising at least one active ingredient based on the calculated transit time and a location of a targeted tissue within the mammalian body.

In yet another embodiment, the foregoing optimization methods may additionally comprise the steps of: calculating a constant based on a length of the first vascular tree, the blood volume of the first vascular tree, and the calculated transit time in the first vascular tree; and using the constant to calculate a second transit time within a second vasculature tree at or near the targeted tissue. In such cases, the step of modifying the composition of a pharmaceutical compound may additionally take into account (be based upon) the calculated second transit time.

Additional exemplary methods comprise methods for diagnosing disease in a mammalian biological tree. In at least one embodiment of such a method, the method comprising the steps of: obtaining a baseline transit time for a model mammalian vascular tree; obtaining a biological tree image showing a vasculature of at least part of a first mammalian vascular tree comprising at least a vessel segment; determining a transit time in the vessel segment; determining a blood volume in the vessel segment; determining a blood volume in a first vascular tree comprising the vessel segment; calculating a first transit time in the first vascular tree based upon the transit time through the vessel segment, the blood volume in the vessel segment, and the blood volume in the first vascular tree; and comparing the baseline transit time with the first transit time in the first vascular tree to determine the extent of vessel and/or organ disease; wherein the model mammalian vascular tree is physiologically comparable to the mammalian vascular tree. Additionally, the foregoing diagnosis method may further comprise the steps of: calculating a constant based on a length of the first vascular tree, the blood volume of the first vascular tree, and the calculated transit time in the first vascular tree; determining a length and a blood volume of a second vascular tree; calculating a second transit time in the second vascular tree based upon the use of the calculated constant; and comparing the first transit time of the first vascular tree with the second transit time of the second vascular tree to determine the extent of vessel and/or organ disease.

BRIEF DESCRIPTION OF THE DRAWINGS

FIG. 6A shows a relationship between resistance and diameter and normalized crown length in symmetric vascular trees for various species, according to at least one embodiment of the present disclosure;

FIG. 6B shows a relationship between resistance and length in symmetric vascular trees for various species, according to at least one embodiment of the present disclosure;

FIG. 7A shows a table of parameters with correlation coefficients calculated from the Marquardt-Levenberg algorithm for various species, according to at least one embodiment of the present disclosure;

FIG. 9 shows a table of parameters B and A in asymmetric coronary trees and corresponding epicardial trees with vessel diameters greater than 1 mm, according to at least one embodiment of the present disclosure;

FIG. 10 shows a table of parameters B and A in various organs, according to at least one embodiment of the present disclosure;

FIG. 11 shows a table of parameter A obtained from nonlinear regression in various organs, according to at least one embodiment of the present disclosure;

FIG. 16 shows a table of bifurcation diameter models and the corresponding physical mechanisms, according to an embodiment of the present disclosure;

FIG. 19 shows a table demonstrating a relationship between $D_m/(D_l+D_s)$ in Y and T bifurcations determined by the HK, Murray, and area-preservation models, according to an embodiment of the present disclosure;

FIG. 20 shows a table of relative errors between bifurcation diameter models and measurements of quantitative coronary bifurcation angiography, according to an embodiment of the present disclosure;

FIG. 21 shows a table of relative errors between bifurcation diameter models and measurements in the left anterior descending artery (LAD) tree of a porcine heart with mother diameters ≥0.5 mm obtained from casts, according to an embodiment of the present disclosure;

FIG. 23 shows an exemplary website to determine an optimal diameter of a bifurcation segment using a data computation system, according to an embodiment of the present disclosure;

DETAILED DESCRIPTION

Figure 1:
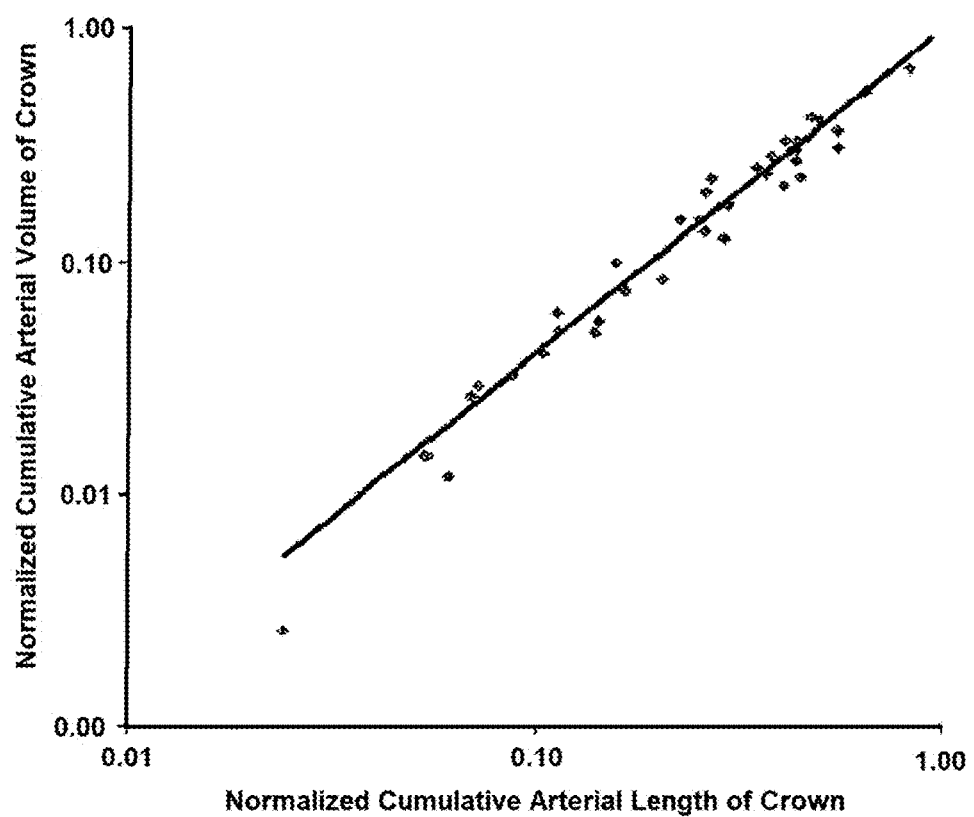
FIG. 1 shows the relation between normalized cumulative arterial volume and corresponding normalized cumulative arterial length for each crown on a log-log plot, according to at least one embodiment of the present disclosure.

The disclosure of the present application provides a framework for an analytical determination of mean transit time in various species and organs throughout the vasculature. Perhaps more specifically, the present disclosure provides novel intraspecific scaling laws for mean transit time in vascular trees. Such scaling laws were formulated and validated in vascular trees (e.g., coronary, pulmonary, mesenteric vessels, skeletal muscle vasculature, and conjunctiva vessels) of various species (e.g., rats, cats, rabbits, pigs, hamsters, and humans) and organs (e.g., heart, lung, mesentery, skeletal muscle, and eye) for which there exists morphometric data, thus demonstrating their accuracy and ease of use. The novel scaling laws provided herein are fundamental to understanding the physiological function of vascular trees to transport blood, which has significant implications for organ and health disease, and the diagnosis and treatment thereof.

For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

Biomimetics (also known as bionics, biognosis, biomimicry, or bionical creativity engineering) is defined as the application of methods and systems found in nature to the study and design of engineering systems and modern technology. The mimic of technology from nature is based on the premise that evolutionary pressure forces natural systems to become highly optimized and efficient. Some examples include (1) the development of dirt- and water-repellent paint from the observation that the surface of the lotus flower plant is practically unsticky, (2) hulls of boats imitating the thick skin of dolphins, and (3) sonar, radar, and medical ultrasound imaging imitating the echolocation of bats.

Microfluidics is the study of the behavior, control and manipulation of microliter and nanoliter volumes of fluids. It is a multidisciplinary field comprising physics, chemistry, engineering and biotechnology, with practical applications to the design of systems in which such small volumes of fluids may be used. Microfluidics is used in the development of DNA chips, micro-propulsion, micro-thermal technologies, and lab-on-a-chip technology.

Regarding the minimum energy hypothesis, the architecture (or manifolds) of the transport network is essential for transport of material in microfluid channels for various chips. The issue is how to design new devices, and more particularly, how to fabricate microfluidic channels that provide a minimum cost of operation. Nature has developed optimal channels (or transport systems) that utilize minimum energy for transport of fluids. The utility of nature's design of transport systems in engineering applications is an important area of biomimetics.

Biological trees (for example, vascular trees) are either used to conduct fluids such as blood, air, bile or urine. Energy expenditure is required for the conduction of fluid through a tree structure because of frictional losses. The frictional losses are reduced when the vessel branches have larger diameters. However, this comes with a cost associated with the metabolic construction and maintenance of the larger volume of the structure. The question is what physical or physiological factors dictate the design of vascular trees. The answer is that the design of vascular trees obeys the "minimum energy hypothesis", i.e., the cost of construction and operation of the vascular system appears to be optimized.

The disclosure of the present application is based on a set of scaling laws determined from a developed minimum energy hypothesis. Equation #1 (the "volume-length relation") demonstrates a relationship between vessel volume, the volume of the entire crown, vessel length, and the cumulative vessel length of the crown:

$$\frac{V}{V_{max}} = \left(\frac{L}{L_{max}}\right)^{\frac{5}{\varepsilon'+1}} \quad (1)$$

In Equation #1, V represents the vessel volume, $V_{max}$ the volume of the entire crown, L represents the vessel length, $L_{max}$ represents the cumulative vessel length of the entire crown, and ε' represents the crown flow resistance, which is equal to the ratio of metabolic to viscous power dissipation.

Equation #2 (the "diameter-length relation") demonstrates a relationship between vessel diameter, the diameter of the most proximal stem, vessel length, and the cumulative vessel length of the crown:

$$\frac{D}{D_{max}} = \left(\frac{L}{L_{max}}\right)^{\frac{3\varepsilon'-2}{4(\varepsilon'+1)}} \quad (2)$$

In Equation #2, D represents the vessel diameter, $D_{max}$ represents the diameter of the most proximal stem, L represents the vessel length, $L_{max}$ represents the cumulative vessel length of the entire crown, and ε' represents the crown flow resistance, which is equal to the ratio of metabolic to viscous power dissipation.

Equation #3 (the "flow rate-diameter relation") demonstrates a relationship between the flow rate of a stem, the flow rate of the most proximal stem, vessel diameter, and the diameter of the most proximal stem:

$$\frac{Q}{Q_{max}} = \left(\frac{D}{D_{max}}\right)^{\frac{4(\varepsilon'+1)}{4\varepsilon'-2}} \quad (3)$$

In Equation #3, Q represents flow rate of a stem, $Q_{max}$ represents the flow rate of the most proximal stem, V represents vessel diameter, $V_{max}$ represents the diameter of the most proximal stem, and ε' represents the crown flow resistance, which is equal to the ratio of metabolic to viscous power dissipation.

Regarding the aforementioned Equations and as used herein, a vessel segment is referred to as a "stem," and the entire tree distal to the stem is referred as a "crown." The aforementioned parameters relate to the crown flow resistance and is equal to the ratio of maximum metabolic-to-viscous power dissipation.

Two additional relations were found for the vascular trees. Equation #4 (the "resistance-length and volume relation") demonstrates a relationship between the crown resistance, the resistance of the entire tree, vessel length, the cumulative vessel length of the crown, vessel volume, and the volume of the entire crown:

$$\frac{R_c}{R_{max}} = \frac{(L/L_{max})^3}{(V/V_{max})^{\varepsilon''}} \quad (4)$$

In Equation #4, $R_c$ represents the crown resistance, $R_{max}$ represents the resistance of the entire tree, L represents vessel length, $L_{max}$ represents the cumulative vessel length of the entire crown, V represents vessel volume, $V_{max}$ represents the volume of the entire crown, and ε' represents the crown flow resistance, which is equal to the ratio of metabolic to viscous power dissipation. Resistance, as referenced herein, is defined as the ratio of pressure differenced between inlet and outlet of the vessel.

Equation #5 (the "flow rate-length relation") demonstrates a relationship between the flow rate of a stem, the flow rate of the most proximal stem, vessel length, the cumulative vessel length of the entire crown:

$$\frac{Q}{Q_{max}} = \frac{L}{L_{max}} \quad (5)$$

In Equation #5, Q represents flow rate of a stem, $Q_{max}$ represents the flow rate of the most proximal stem, L represents vessel length, and $L_{max}$ represents the cumulative vessel length of the entire crown.

In at least one embodiment of the disclosure of the present application, the application of one or more of the aforementioned Equations to acquired vessel data may be useful diagnose and/or aid in the diagnosis of disease.

By way of example, the application of one or more of the aforementioned Equations are useful to diagnose DCAD. For such a diagnosis, the applications of Equations #1-#3 may provide the "signatures" of normal vascular trees and impart a rationale for diagnosis of disease processes. The self-similar nature of these laws implies that the analysis can be carried out on a partial tree as obtained from an angiogram, a computed tomography (CT) scan, or magnetic resonance imaging (MRI). Hence, the application of these Equations to the obtained images may serve for diagnosis of vascular disease that affect the lumen dimension, volume, length (vascularity) or perfusion (flow rate). Additionally, the fabrication of the microfluidic channels can be governed by Equations #1-#5 to yield a system that requires minimum energy of construction and operation. Hence, energy requirements will be at a minimum to transport the required microfluidics.

In one exemplary embodiment, the application of the volume-length relation (Equation #1) to actual obtained images is considered as shown in FIG. 1. First, images (angiograms in this example) of swine coronary attics were obtained. The application of Equation #1 on various volumes and lengths from the angiograms resulted in the individual data points shown within FIG. 1 (on a logarithmic scale). The line depicted within FIG. 1 represents the mean of the data points (the best fit) among the identified data points.

Figure 2:
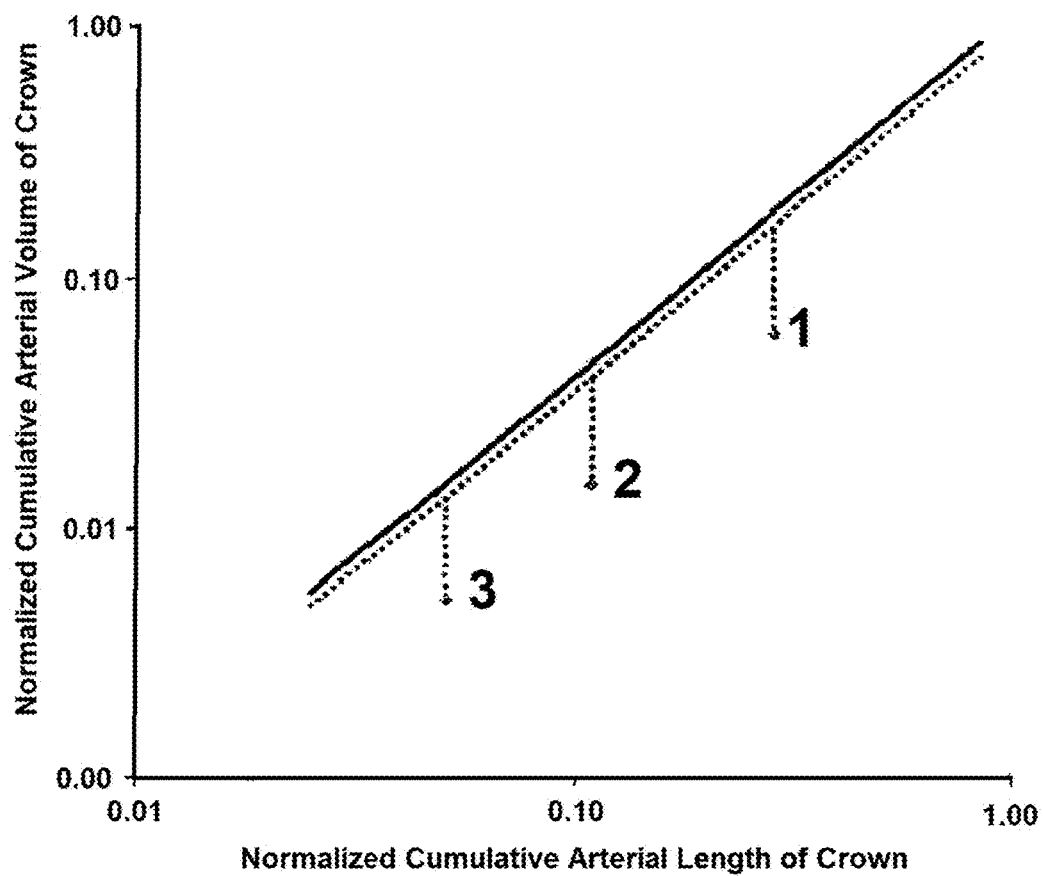
FIG. 2 shows the presence of DCAD at locations along the mean trend lines for normal (solid) and DCAD vasculature (broken) according to at least one embodiment of the present disclosure.

In FIG. 2, the mean of the data (solid line) is compared to an animal with diffuse disease at three different vessel sizes: proximal (1), middle (2), and distal (3). The reductions in volume shown on FIG. 2 correspond to approximately 40% stenosis, which is typically undetectable with current methodologies. At each diffuse stenosis, the length remains constant but the diameter (cross-sectional, and hence, volume) changes. The length is unlikely to change unless the flow becomes limiting (more than approximately 80% stenosis) and the vascular system experiences vessel loss (rarefication) and remodeling. It is clear that a 40% stenosis deviates significantly from the y-axis (as determined by statistical tests) from the normal vasculature, and as such, 40% stenosis can be diagnosed by the system and method of the disclosure of the present application. It can be appreciated that the disclosure of the present application can predict inefficiencies as low as about 10%, compared to well-trained clinicians who can only predict inefficiencies at about 60% at best.

This exemplary statistical test compares the deviation of disease to normality relative to the variation within normality. The location of the deviation along the x-axis corresponds to the size of the vessel. The vessel dimensions range as proximal>mid>distal. Hence, by utilizing the system and method of the disclosure of the present application, the diagnosis of the extent of disease and the dimension of the vessel branch is now possible. Similar embodiments with other scaling relations as described herein can be applied similarly to model and actual vascular data.

The techniques disclosed herein have tremendous application in a large number of technologies. For example, a software program or hardware device may be developed to diagnose the percentage of inefficiency (hence, occlusion) in a circulatory vessel or system.

Figure 3:
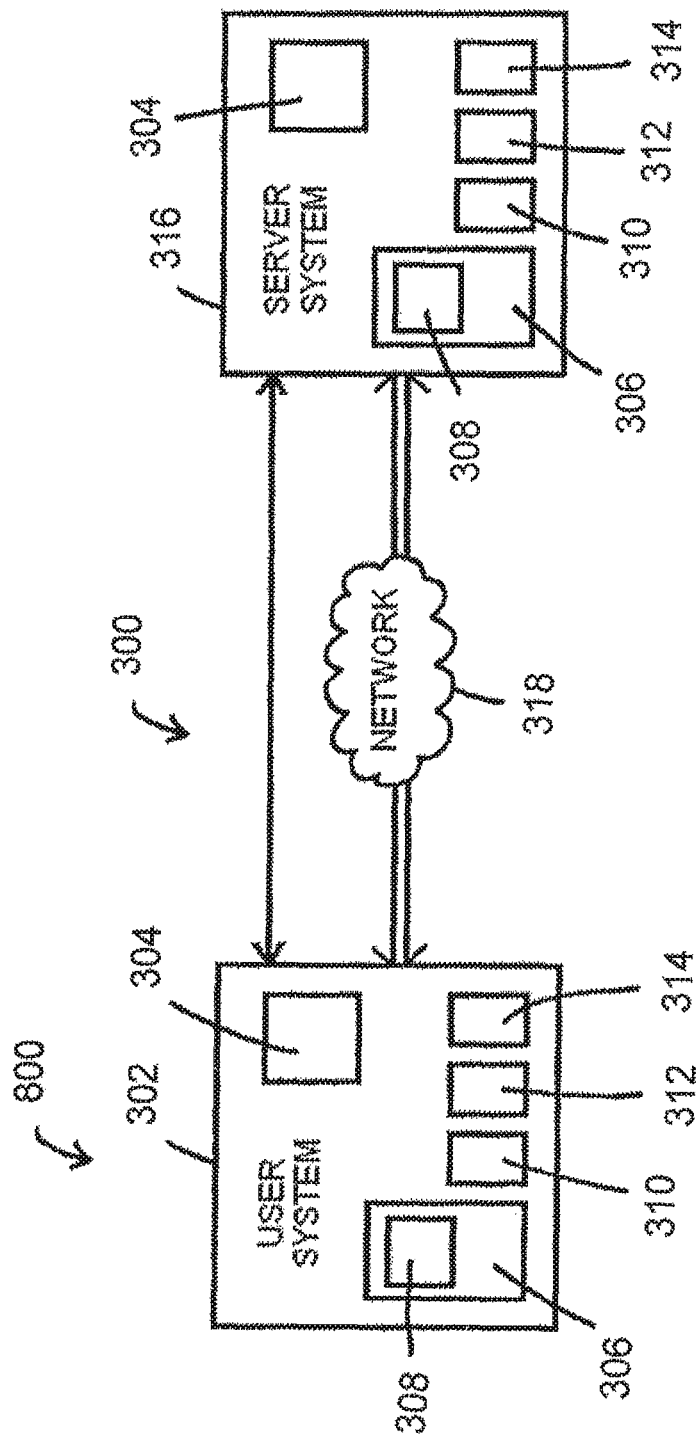
FIG. 3 shows a diagnostic system and/or a data computation system according to at least one embodiment of the present disclosure.

Regarding the computer-assisted determination of such diagnoses, an exemplary system of the disclosure of the present application is provided. Referring now to FIG. 3, there is shown a diagrammatic view of an embodiment of diagnostic system 300 of the present disclosure. In the embodiment shown in FIG. 3, diagnostic system 300 comprises user system 302. In this exemplary embodiment, user system 302 comprises processor 304 and one or more storage media 306. Processor 304 operates upon data obtained by or contained within user system 302. Storage medium 306 may contain database 308, whereby database 308 is capable of storing and retrieving data. Storage media 306 may contain a program (including, but not limited to, database 308), the program operable by processor 304 to perform a series of steps regarding data relative of vessel measurements as described in further detail herein.

Any number of storage media 306 may be used with diagnostic system 300 of the present disclosure, including, but not limited to, one or more of random access memory, read only memory, EPROMs, hard disk drives, floppy disk drives, optical disk drives, cartridge media, and smart cards, for example. As related to user system 302, storage media 306 may operate by storing data relative of vessel measurements for access by a user and/or for storing computer instructions. Processor 304 may also operate upon data stored within database 308.

Regardless of the embodiment of diagnostic system 300 referenced herein and/or contemplated to be within the scope of the present disclosure, each user system 302 may be of various configurations well known in the art. By way of example, user system 302, as shown in FIG. 3, comprises keyboard 310, monitor 312, and printer 314. Processor 304 may further operate to manage input and output from keyboard 310, monitor 312, and printer 314. Keyboard 310 is an exemplary input device, operating as a means for a user to input information to user system 302. Monitor 312 operates as a visual display means to display the data relative of vessel measurements and related information to a user using a user system 302. Printer 314 operates as a means to display data relative of vessel measurements and related information. Other input and output devices, such as a keypad, a computer mouse, a fingerprint reader, a pointing device, a microphone, and one or more loudspeakers are contemplated to be within the scope of the present disclosure. It can be appreciated that processor 304, keyboard 310, monitor 312, printer 314 and other input and output devices referenced herein may be components of one or more user systems 302 of the present disclosure.

It can be appreciated that diagnostic system 300 may further comprise one or more server systems 316 in bidirectional communication with user system 302, either by direct communication (shown by the single line connection on FIG. 3), or through a network 318 (shown by the double line connections on FIG. 3) by one of several configurations known in the art. Such server systems 316 may comprise one or more of the features of a user system 302 as described herein, including, but not limited to, processor 304, storage media 306, database 308, keyboard 310, monitor 312, and printer 314, as shown in the embodiment of diagnostic system 300 shown in FIG. 3. Such server systems 316 may allow bidirectional communication with one or more user systems 302 to allow user system 302 to access data relative of vessel measurements and related information from the server systems 316. It can be appreciated that a user system 302 and/or a server system 316 referenced herein may be generally referred to as a "computer."

Figure 4:
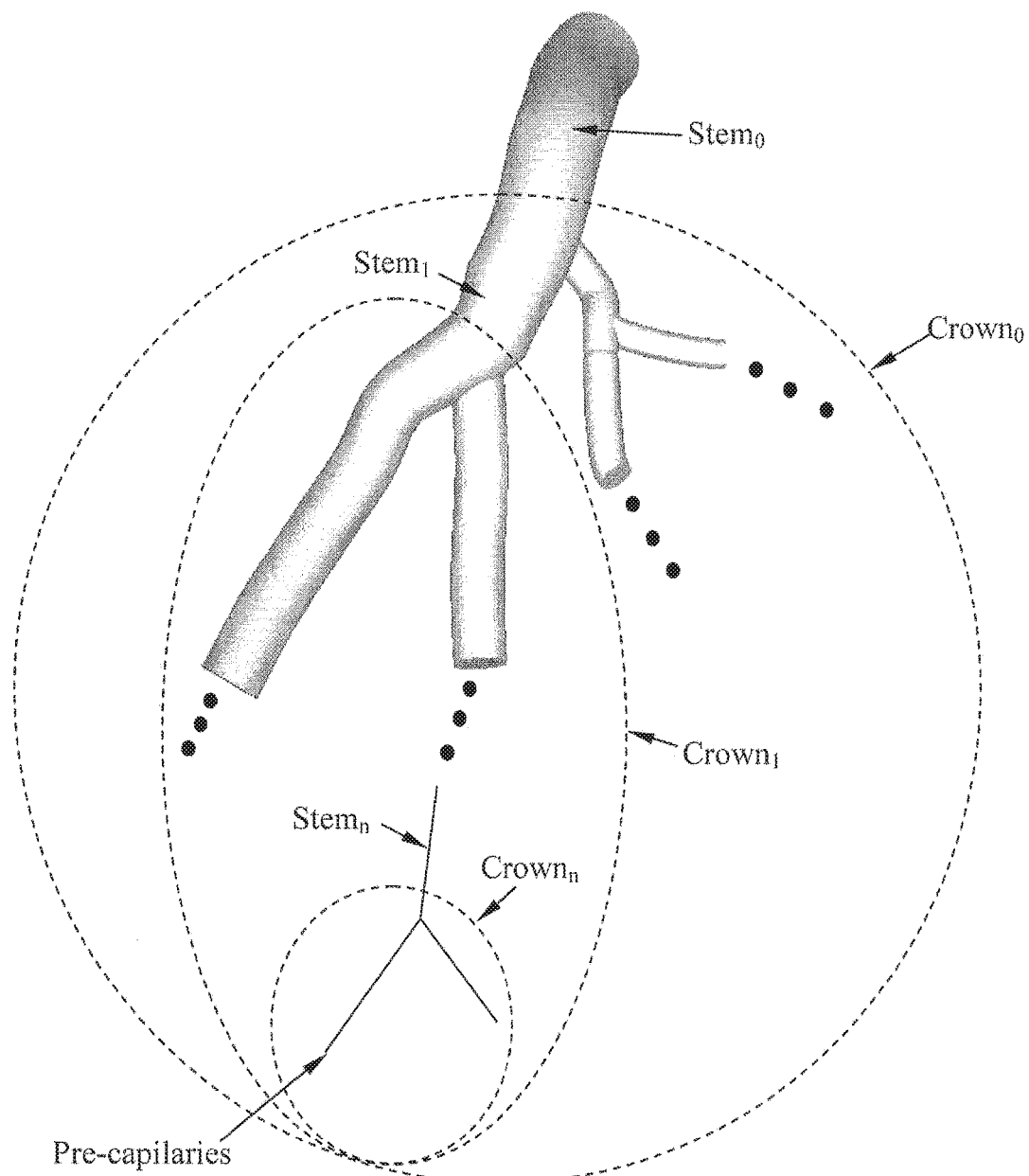
FIG. 4 shows an illustration of a definition of a stem-crown unit according to at least one embodiment of the present disclosure.

Several concepts are defined to formulate resistance scaling laws of the disclosure of the present application. A vessel segment is defined as a "stem" and the entire tree distal to the stem is defined as a "crown," as shown in FIG. 4 and as previously disclosed herein. FIG. 4 shows a schematic illustration of the definition of the stem-crown unit. Three stem-crown units are shown successively (1, 2, and n), with the smallest unit corresponding to an arteriole-capillary or venule-capillary unit. An entire vascular tree, or substantially the entire vascular tree, consists of many stem-crown units down to, for example, the smallest arterioles or venules. In one exemplary embodiment of the disclosure of the present application, the capillary network (referenced herein as having vessel diameters of less than 8 microns) is excluded from the analysis because it is not tree-like in structure. A stem, for purposes of simplification, is assumed to be a cylindrical tube with no consideration of vessel tapering and other nonlinear effects as they play a relatively minor role in determining the hemodynamics of the entire tree. However, the disclosure of the present application is not intended to be limited by the aforementioned capillary network exclusion and/or the aforementioned stem assumption.

Through the Hagen-Poiseuille law known in the art, the resistance of the steady laminar flow in a stem of an entire tree may be provided as shown in Equation #6:

$$R_s = \frac{\Delta P_s}{Q_s} \tag{6}$$

In Equation #6, $R_s$ is the resistance of a stem segment, $\Delta P_s$ is the pressure gradient along the stem, and $Q_s$ is a volumetric flow rate through the stem.

According to the disclosure of the present application, Equation #6, providing for $R_s$, may be written in a form considering stem length and diameter, as shown in Equation #7.

$$R_s = \frac{128 \, \mu L_s}{\pi D_s^4} = K_s \frac{L_s}{D_s^4} \tag{7}$$

In Equation #7, $R_s$ is the resistance of a stem segment, $L_s$ is the length of the stem, $D_s$ is the diameter of the stem, $\mu/\pi$ the viscosity of a fluid, and $K_s$ is a constant equivalent to $128\mu/\pi$.

Furthermore, the resistance of a crown may be demonstrated as shown in Equation #8:

$$R_c = \frac{\Delta P_c}{Q_s} \quad (8)$$

In Equation #8, $R_c$ is the crown resistance, $\Delta P_s$ is the pressure gradient in the crown from the stem to the terminal vessels, and $Q_s$ is a volumetric flow rate through the stem. Equation #8 may also be written in a novel form to solve for $R_c$ in accordance with the disclosure of the present application as shown in Equation #9:

$$R_c = K_c \frac{L_c}{D_s^4} \quad (9)$$

In Equation #9, $R_c$ is the crown resistance, $L_c$ is the crown length, $D_s$ is the diameter of the stem vessel proximal to the crown, and $K_c$ is a constant that depends on the branching ration, diameter ratio, the total number of tree generations, and viscosity in the crown. The crown length, $L_c$, may be defined as the sum of the lengths of each vessel in the crown (or substantially all of the vessels in the crown).

As Equation #9, according to the disclosure of the present application, is applicable to any stem-crown unit, one may obtain the following equation:

$$R_{max} = K_c \frac{L_{max}}{D_{max}^4} \quad (10)$$

so that the following formula for $K_c$ may be obtained:

$$K_c = \frac{R_{max} \cdot D_{max}^4}{L_{max}} \quad (11)$$

$D_{max}$, $L_{max}$, and $R_{max}$ correspond to the most proximal stem diameter, the cumulative vascular length, and total resistance of the entire tree, respectively. In the non-dimensional form, Equation #11 can be written as:

$$\left(\frac{R_c}{R_{max}}\right) \cdot \left(\frac{D_s}{D_{max}}\right)^4 = A_1 \left(\frac{L_c}{L_{max}}\right) \quad (12)$$

Parameter $A_1$ in Equation #12, as provided above, should be equal to one. From Equations #7 and #9, one may then obtain the desired resistance scaling relation between a single vessel (a stem) and the distal crown tree:

$$\left(\frac{R_s}{R_c}\right) = \frac{K_s}{K_c}\left(\frac{L_s}{L_c}\right) \quad (13)$$

Equations #7-13 relate the resistance of a single vessel to the corresponding distal tree.

Verification. The asymmetric coronary arterial trees of hearts and symmetric vascular trees of many organs were used to verify the proposed resistance scaling law. First, the asymmetric coronary arterial tree has been reconstructed in pig hearts by using the growth algorithm introduced by Mittal et al. (A computer reconstruction of the entire coronary arterial tree based on detailed morphometric data. Ann. Biomed. Eng. 33 (8):1015-1026 (2005)) based on measured morphometric data of Kassab et al. (Morphometry of pig coronary arterial trees. Am J Physiol Heart Circ Physiol. 265:H350-H365 (1993)). Briefly, vessels greater than or equal to 40 μm were reconstructed from cast data while vessels <40 μm were reconstructed from histological data. After the tree was reconstructed, each vessel was assigned by diameter-defined Strahler orders which was developed based on the Strahler system (Strahler, A. N. Hypsometric (area altitude) analysis of erosional topology. Bull Geol Soc Am. 63:1117-1142 (1952)).

Furthermore, symmetric vascular trees of many organs were constructed in the Strahler system, based on the available literature. Here, the pulmonary arterial tree of rats was obtained from the study of Jiang et al. (Diameter-defined Strahler system and connectivity matrix of the pulmonary arterial tree. J. Appl. Physiol. 76:882-892 (1994)); the pulmonary arterial/venous trees of cats from Yen et al. (Morphometry of cat's pulmonary arterial tree. J Biomech. Eng. 106:131-136 (1984) and Morphometry of cat pulmonary venous tree. J. Appl. Physiol. Respir. Environ. Exercise. Physiol. 55:236-242 (1983)); the pulmonary arterial trees of humans from Singhal et al. (Morphometric study of pulmonary arterial tree and its hemodynamics, J. Assoc. Physicians India. 21:719-722 (1973) and Morphometry of the human pulmonary arterial tree. Circ. Res. 33:190 (1973)) and Huang et al. (Morphometry of the human pulmonary vasculature. J. Appl. Physiol. 81:2123-2133 (1996)); the pulmonary venous trees of humans from Horsfield et al. (Morphometry of pulmonary veins in man. Lung. 159:211-218 (1981)) and Huang et al.; the skin muscle arterial tree of hamsters from Bertuglia et al. (Hypoxia- or hyperoxia-induced changes in arteriolar vasomotion in skeletal muscle microcirculation. Am J Physiol Heart Circ Physiol. 260: H362-H372 (1991)); the retractor muscle arterial tree of hamsters from Ellsworth et al. (Analysis of vascular pattern and dimensions in arteriolar networks of the retractor muscle in young hamsters. Microvasc. Res. 34:168-183 (1987)); the mesentery arterial tree of rats from Ley et al. (Topological structure of rat mesenteric microvessel networks. Microvasc. Res. 32:315-332 (1986)); the sartorius muscle arterial tree of cats from Koller et al. (Quantitative analysis of arteriolar network architecture in cat sartorius muscle. Am J Physiol Heart Circ Physiol. 253: H154-H164 (1987)); and the bulbular conjunctiva arterial/venous trees of humans and the omentum arterial tree of rabbits from Fenton et al. (Microcirculatory model relating geometrical variation to changes in pressure and flow rate. Ann. Biomed. Eng. 1981; 9:303-321 (1981)).

Data analysis. For the asymmetric coronary arterial trees, full tree data are presented as log-log density plots showing the frequency of data because of the enormity of data points, i.e., darkest shade reflects highest frequency or density and the lightest shade reflects the lowest frequency. The nonlinear regression (SigmaStat 3.5) is used to analyze the data in both asymmetric and symmetric tree, which uses the Marquardt-Levenberg algorithm (nonlinear regression) to find the coefficients (parameters) of the independent variables that give the "best fit" between the equation and the data.

Results: Validation of resistance scaling law in entire vascular trees. The predictions of these novel scaling laws were then validated in both the asymmetric coronary trees and the symmetric vascular trees for which there exists morphometric data in the literature (e.g., vessels of various skeletal muscles, mesentery, omentum, and conjunctiva).

Figure 5A:
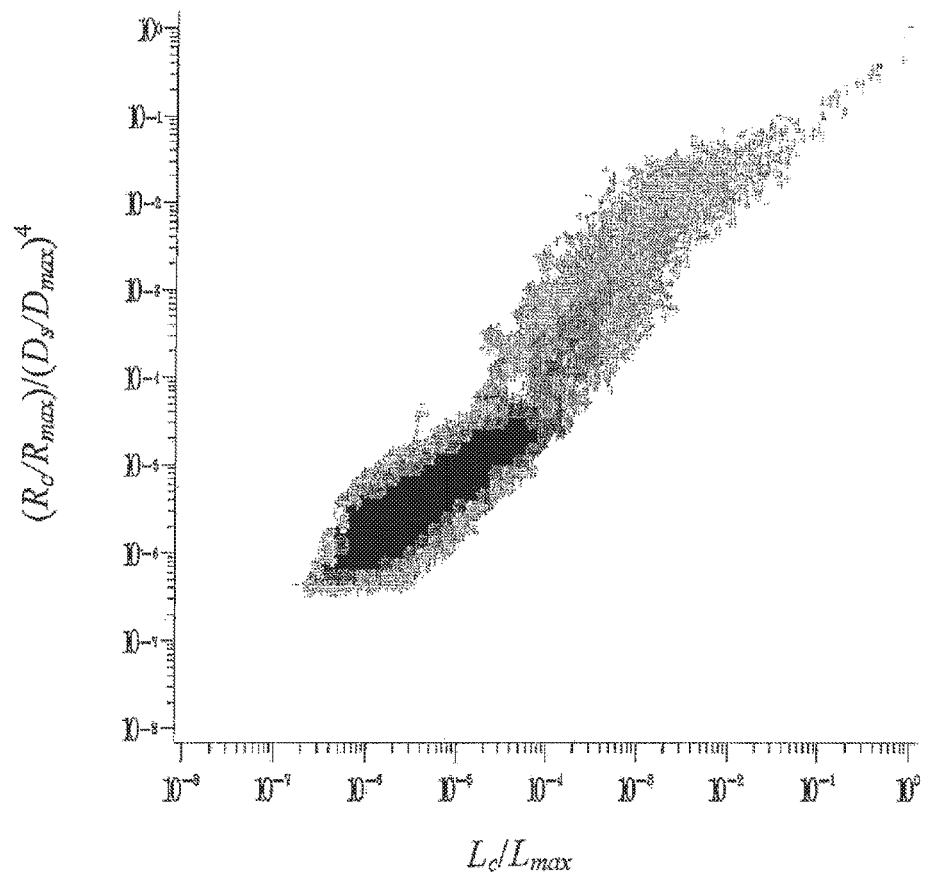
FIGS. 5A-5C show relationships between resistance and diameter and normalized crown length of LAD, LCx, and RCA trees of a pig, respectively, according to at least one embodiment of the present disclosure.
Figure 5B:
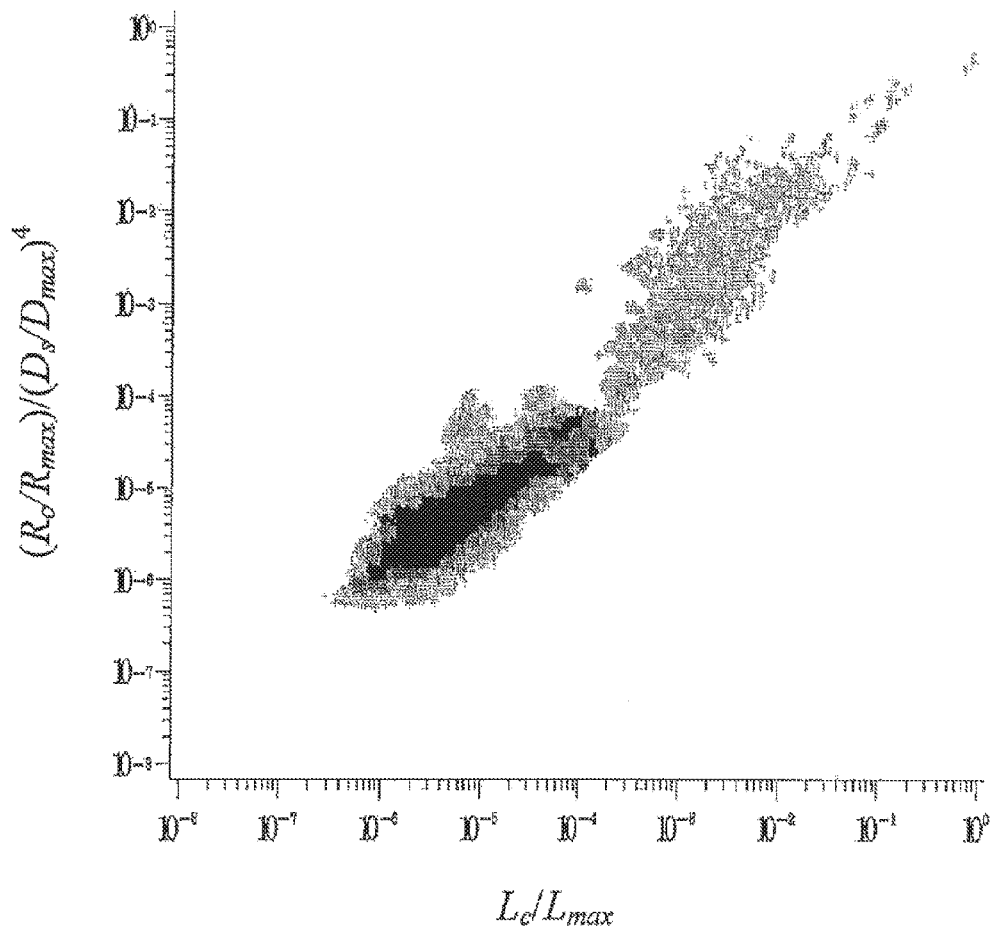
Figure 5C:
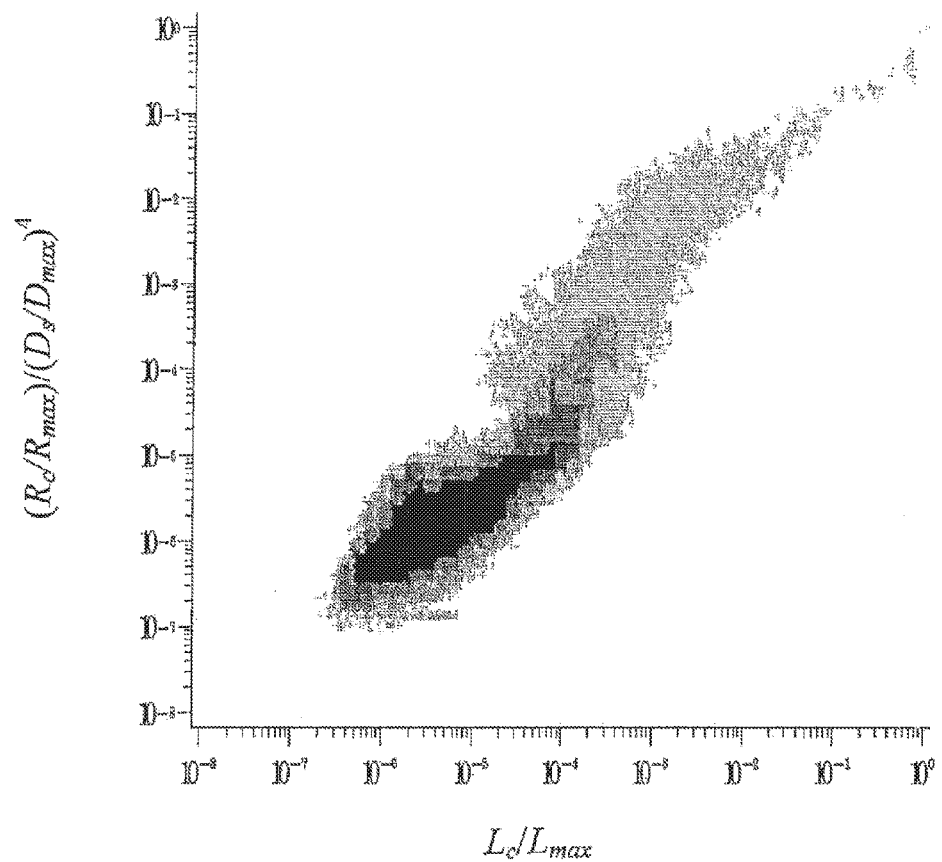
Figure 5D:
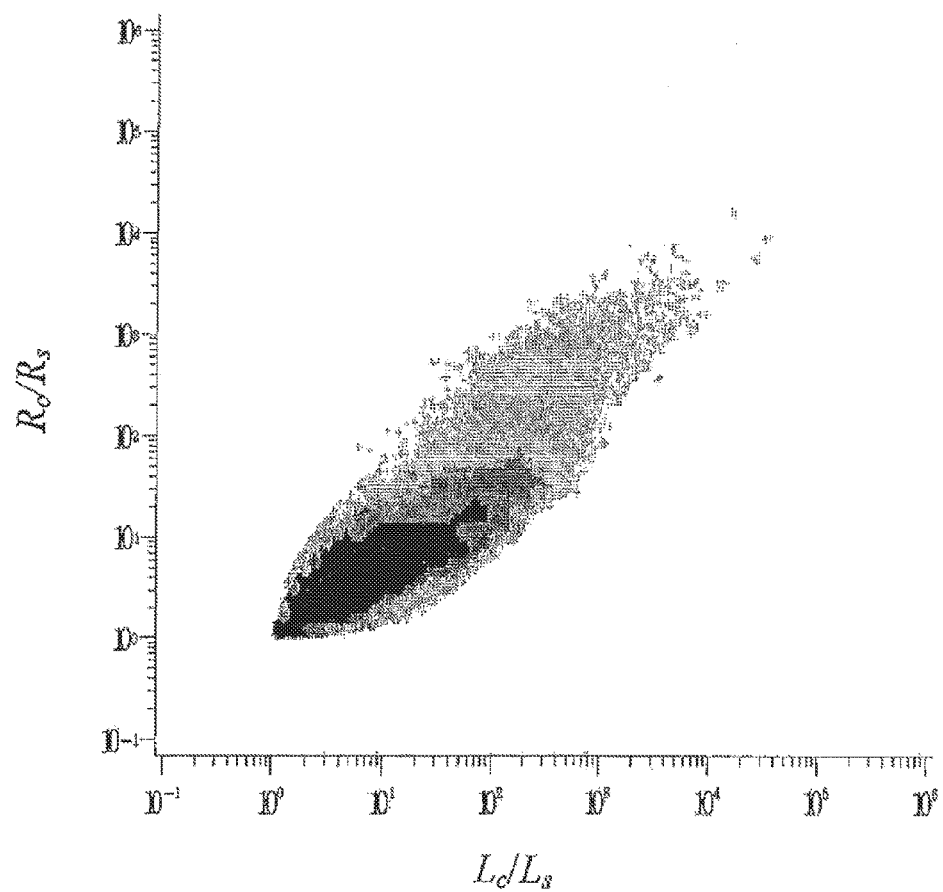
FIGS. 5D-5F show relationships between resistance and length of LAD, LCx, and RCA trees of a pig, respectively, according to at least one embodiment of the present disclosure.
Figure 5E:
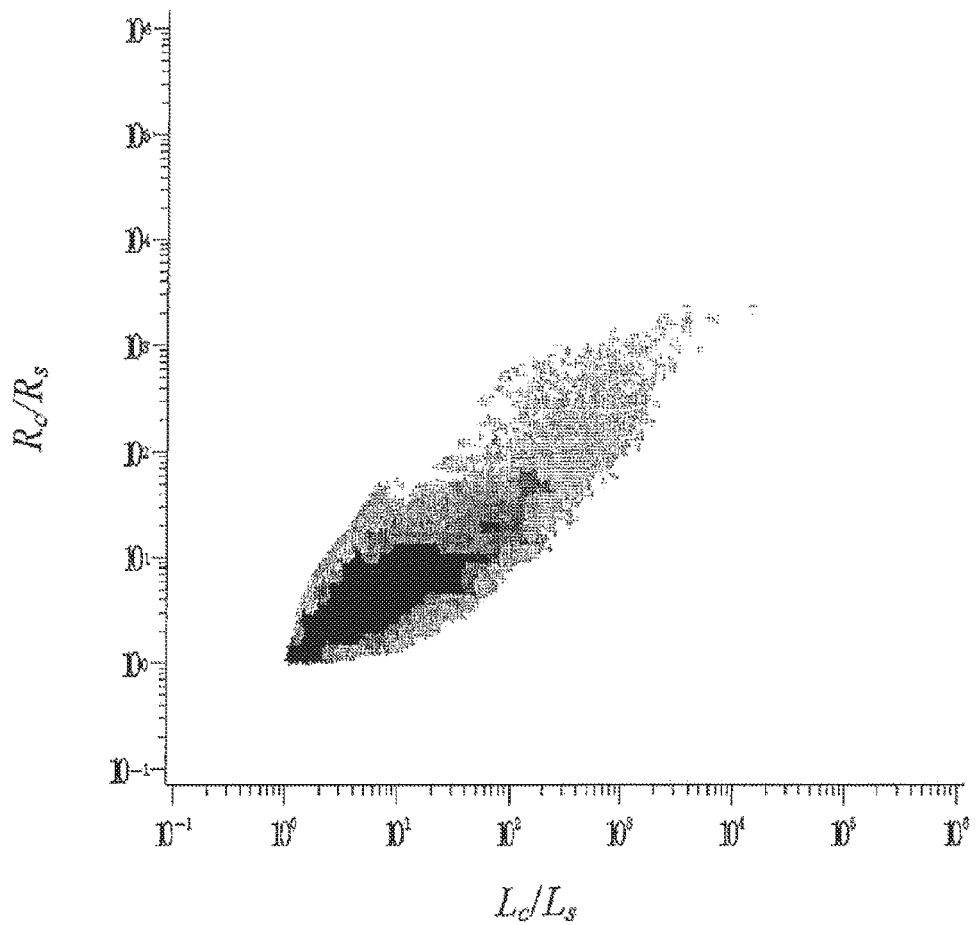
Figure 5F:
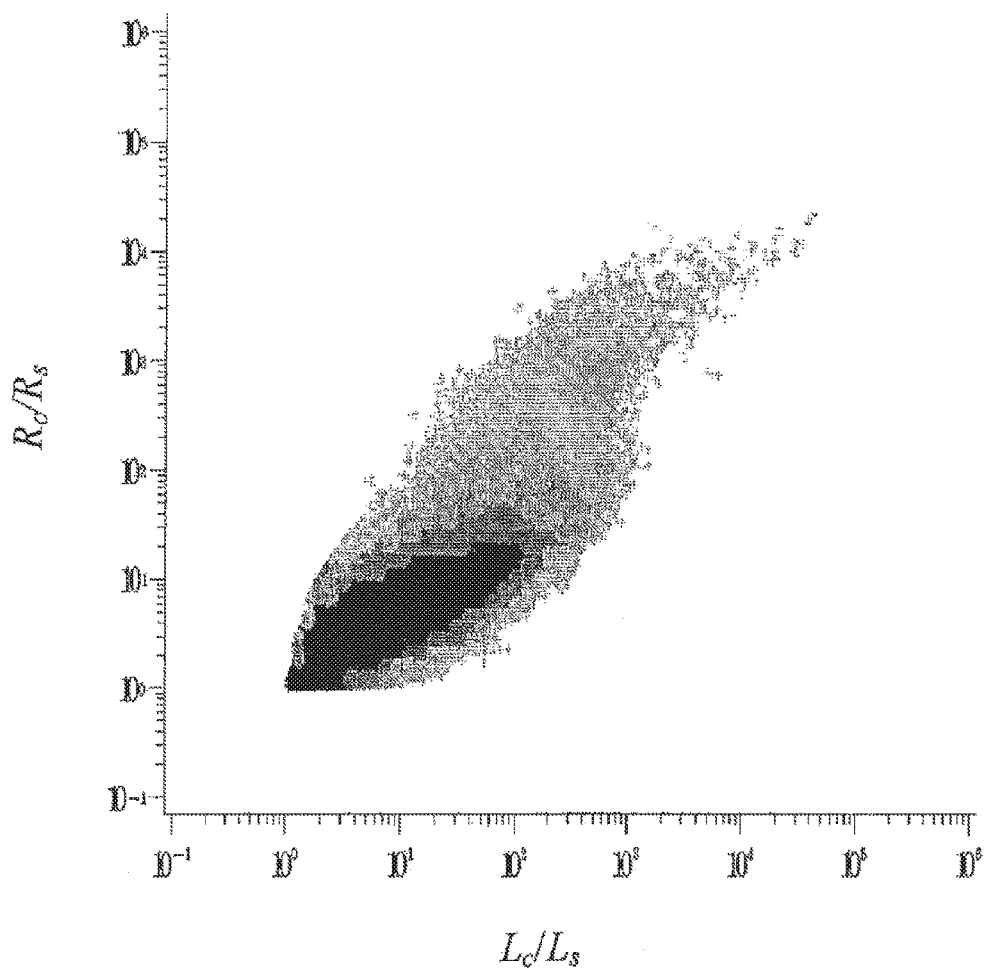

First, the entire asymmetric coronary LAD, LCx, and RCA trees with several millions of vessels were analyzed (15, 16). FIGS. 5A, 5B, and 5C show a log-log plot of $(R_c/R_{max})(D_s/D_{max})^4$ as a function of normalized crown length $(L_c/L_{max})$ for LAD, LCx, and RCA trees, respectively. Relationships between $(R_c/R_{max})(D_s/D_{max})^4$ and normalized crown length $(L_c/L_{max})$ in the asymmetric entire LAD (FIG. 5A), LCx (FIG. 5B), and RCA (FIG. 5C) trees of pig, which include 946937, 571383, and 836712 stem-crown units are shown, respectively. Through the Marquardt-Levenberg algorithm with the exponents of $L_c/L_{max}$ constrained to one, parameter $A_1$ in Equation #12 has a value of 1.027 ($R^2$=0.990), 0.993 ($R^2$=0.997), and 1.084 ($R^2$=0.975) for LAD, LCx, and RCA trees, respectively. The values of $A_1$ obtained from morphometric data are in agreement with the theoretical value of one. Corresponding to FIGS. 5A, 5B, and 5C, FIGS. 5D, 5E, and 5F show a log-log plot of $R_c/R_s$ as a function of $L_c/L_s$. Parameter $K_s/K_c$ in Equation #13 has a value of 2.647 ($R^2$=0.954), 2.943 ($R^2$=0.918), and 2.147 ($R^2$=0.909) for LAD, LCx, and RCA trees, respectively. FIGS. 5D, 5E, and 5F show a relationship between $R_c/R_s$ and $L_c/L_s$ in the LAD, LCx, and RCA trees of pig, corresponding to FIGS. 5A, 5B, and 5C.

Figure 7B:
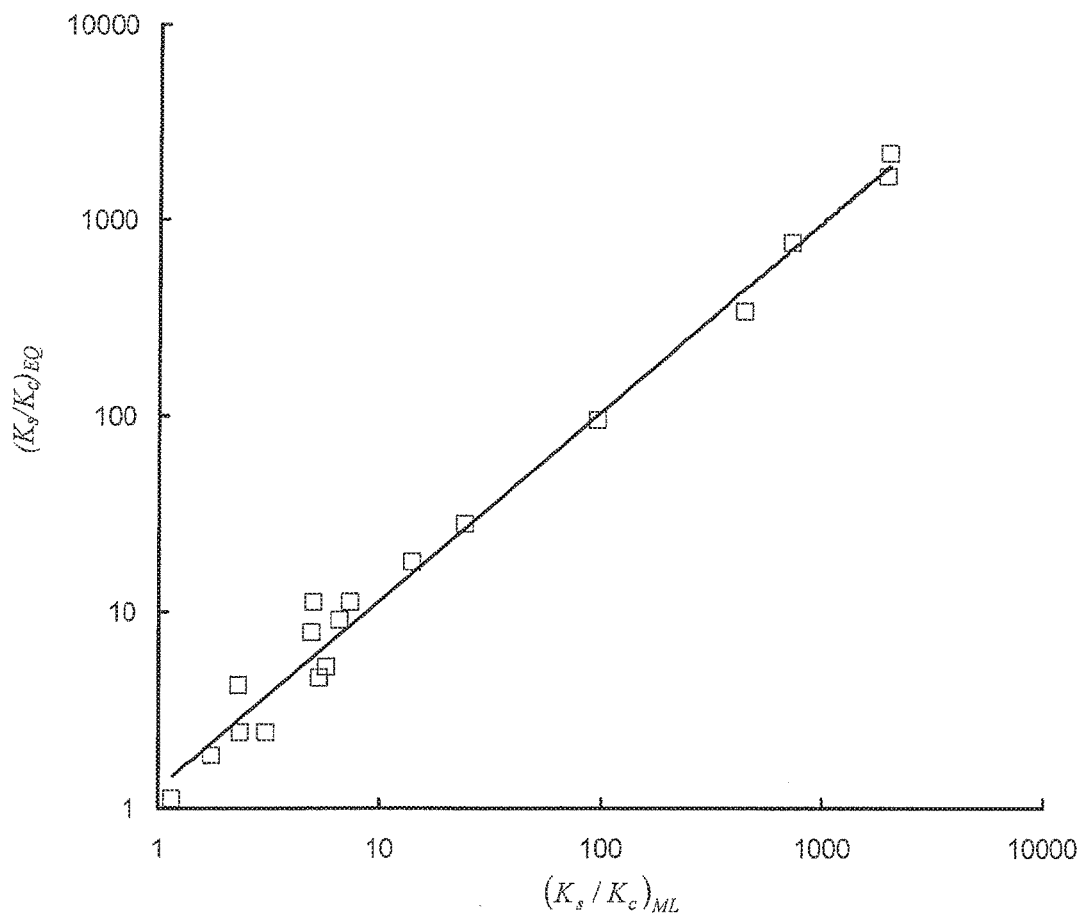
FIG. 7B shows a comparison of data from nonlinear regression and equations of the present disclosure; according to at least one embodiment of the present disclosure.

Furthermore, FIGS. 6A and 6B show the log-log plots of $(R_c/R_{max})(D_0/D_{max})^4$ and $R_c/R_s$ as a function of $L_c/L_{max}$ and $L_c/L_s$, respectively, in the vascular trees of various species. Corresponding to FIGS. 6A and 6B, the Marquardt-Levenberg algorithm was used to calculate the parameters $A_1$ and $K_s/K_c$ in Equations #12 and #13, respectively, while the exponents of $L_c/L_{max}$ and $L_c/L_s$ were constrained to be one. Parameters $A_1$ in Equation #12 and $K_s/K_c$ in Equation #13 with correlation coefficient for various species are listed in the table shown in FIG. 7A. The data in FIG. 7A have a mean value (averaged over all organs and species) of 1.01±0.06 for parameter $A_1$. FIG. 7B shows a comparison of $(K_s/K_c)_{ML}$ from the nonlinear regression of anatomical data and $(K_s/K_c)_{EQ}$ based on Equations $K_s=128\rho/\pi$ and $$K_c = \frac{R_{max} \cdot D_{max}^4}{L_{max}},$$

noting that the comparison can be represented as $$\left(\frac{K_s}{K_c}\right)_{EQ} = A \cdot \left(\frac{K_s}{K_c}\right)_{ML}^B,$$

When A is constrained to be one in the Marquardt-Levenberg algorithm, B has a value of one ($R^2$=0.983). Using the same Marquardt-Levenberg algorithm, a nonlinear regression fit of all raw data yields a mean of 1.01 ($R^2$=0.95) for parameter $A_1$. Both the mean value and the nonlinear regression fit of all data agree with the theoretical value of one.

FIG. 6B shows much smaller $R_c/R_s$ in pulmonary vascular tree than other organs at the same value of $L_c/L_s$. Accordingly, the $K_s/K_c$ values (shown in the table in FIG. 7A) are similar except for the pulmonary vasculature with a larger value. The $K_s/K_c$ values are also calculated based on Equations $K_s=128\mu/\pi$ and $K_c=R_{max}D_{max}^4/L_{max}$, which is compared with the $K_s/K_c$ values obtained from the Marquardt-Levenberg algorithm, as shown in FIG. 7B. The viscosity is determined based on an empirical in vivo relation that depends on the vessel diameter. The comparison shows good agreement. The $K_s/K_c$ values in the pulmonary vasculature have a larger value because the cross-section area of pulmonary tree has a large increase from proximal to terminal vessels in the pulmonary tree and the resistance of the entire tree ($R_{max}$) is much smaller. The agreement between experimental measurement and theoretical relations illustrate that the novel resistance scaling law disclosed herein of Equations #9, #12, and #13 can be applied to a general vascular tree down to the smallest arterioles or venules.

Figure 8A:
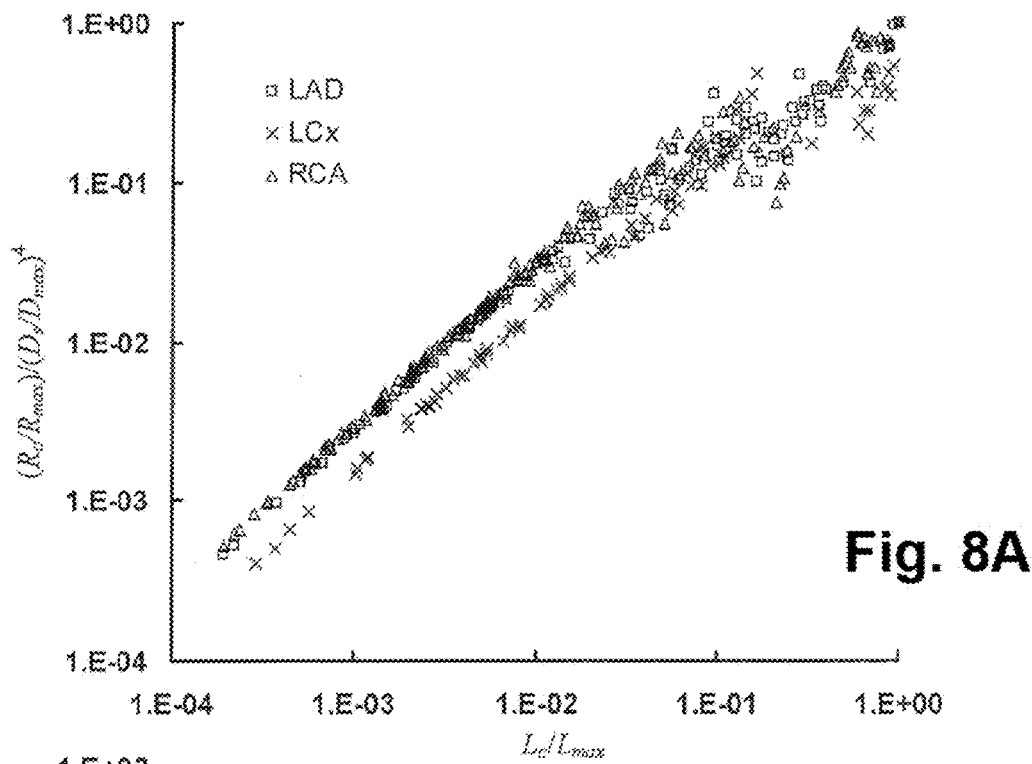
FIG. 8A shows a relationship between resistance and diameter and normalized crown length in the LAD, LCx, and RCA epicardial trees of a pig, respectively, according to at least one embodiment of the present disclosure.
Figure 8B:
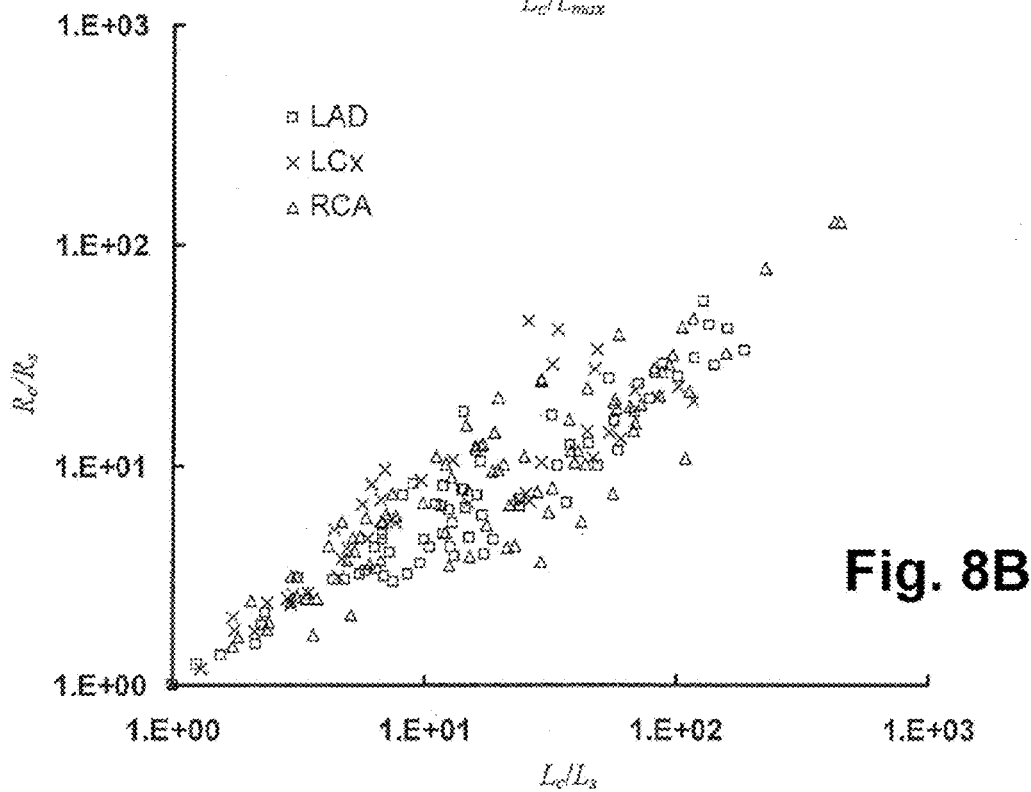
FIG. 8B shows a relationship between resistance and length in the LAD, LCx, and RCA epicardial trees of a pig, respectively, according to at least one embodiment of the present disclosure.

Results: Resistance scaling law of partial vascular trees. FIGS. 8A and 8B show the relations between $(R_c/R_{max})(D_s/D_{max})^4$ and normalized crown volume $(L_c/L_{max})$ and between $R_c/R_s$ and $L_c/L_s$, respectively, in the LAD, LCx, and RCA epicardial trees. FIG. 8A shows a relationship between $(R_c/R_{max})(D_s/D_{max})^4$ and normalized crown volume $(L_c/L_{max})$ in the LAD, LCx, and RCA epicardial trees of pig with diameter of mother vessels larger than 1 mm, which include 132, 90, and 192 vessel segments, respectively. FIG. 8B shows a relationship between $R_c/R_s$ and $L_c/L_s$ in the LAD, LCx, and RCA epicardial trees of pig corresponding to FIG. 8A. Parameter $A_1$ in Equation #12 has a value of 0.902 ($R^2$=0.907), 0.895 ($R^2$=0.887), and 1.000 ($R^2$=0.888) and parameter $K_s/K_c$ in Equation #13 has a value of 3.29 ($R^2$=0.875), 3.48 ($R^2$=0.816), and 3.12 ($R^2$=0.927) for the LAD, LCx, and RCA epicardial trees, respectively.

The aforementioned study validates the novel resistance scaling law of the present disclosure that relates the resistance of a vessel branch to the equivalent resistance of the corresponding distal tree in various vascular trees of different organs and species. The significance of the resistant scaling law is that the hydraulic resistance of a distal vascular tree can be estimated from the proximal vessel segment. As a result, the disclosure of the present application has wide implications from understanding fundamental vascular design to diagnosis of disease in the vascular system.

Resistance scaling law. The mechanisms responsible for blood flow regulation in vascular trees are of central importance, but are still poorly understood. The arteriolar beds are the major site of vascular resistance, which contributes to the maintenance and regulation of regional blood flow. Although arteriolar resistance plays an important role in the etiology of many diseases, in particular, hypertension, it has been difficult to predict the resistance in the arteriolar beds. The novel resistance scaling law of the present disclosure addresses this issue.

The resistance scaling laws (Equations #9, #12, and #13) are derived based on the relation of diameter ratio (DR=$D_i/D_{i-1}$), length ratio (LR=$L_i/L_{i-1}$) and branching ratio (BR=$N_i/N_{i-1}$) in a symmetric tree as:

$$DR = BR^{-\frac{1}{2+\varepsilon}} \text{ and } LR = BR^{-\frac{1}{3}},$$

where $\varepsilon=0$ and $\varepsilon=1$ represent the area-preservation, $\pi D_{i-1}^2 = BR \cdot \pi D_i^2$, and Murray's law, $\pi D_{i-1}^3 = BR \cdot \pi D_i^3$, respectively.

Although the total cross-sectional area (CSA) may increase dramatically from the aorta to the arterioles, the variation is significantly smaller in most organs except for the lung. The increase of CSA towards the capillaries is typically inferred from the decrease in velocity. The velocity between the most proximal and distal levels in various organs of mammals is found to vary by about a factor of five, except for the pulmonary vascular trees. This is clearly reflected by the table shown in FIG. 7A, in which $$K_s/K_c = \frac{1}{K_\varepsilon}$$

is relatively small except for the pulmonary vasculature. This implies that wall shear stress (WSS) increases from the arteries to the arterioles in most organs, which is consistent with previous measurements.

Structure-function scaling laws obtained from resistance scaling law. A mathematical model (the ¾-power scaling law) was derived in a symmetric vasculature to characterize the allometric scaling laws, based on the minimum energy theory. The ¾-power scaling law can be written as $Q_s \alpha M^{3/4}$, where $Q_s$ is the volumetric flow rate of the aorta and M is body mass. In a stem-crown unit, $Q_s$ is the volumetric flow rate of the stem and M is the mass perfused by the stem crown unit. The volumetric flow rate of the stem is $Q_s = \pi D_s^2 U_s / 4$, where $D_s$ and $U_s$ are the diameter and the mean flow velocity of the stem (averaged over the cross-section of stem). Similar to at least one known model, the pressure drop from the stem to the capillaries $\Delta P_c$ and the mean flow velocity of the stem ($U_s$) are independent of the perfused mass so that $D_s \alpha M^{3/8}$ and the resistance of the crown ($R_c = \Delta P_c / Q_s$) is inversely proportional to the volumetric flow rate ($R_c \alpha Q_{s-1} \alpha M^{-3/4}$). Since $D_s \alpha M^{3/8}$, $R_c \alpha M^{-3/4}$, and $K_c$ is a constant, Equations #9 and #12 yields that the crown length $L_c \alpha M^{3/4}$. The cumulative length-mass scaling in pig hearts, $L_c \alpha M^{3/4}$, has recently been verified by the present inventors and their research group. This relation, in conjunction with the flow-mass relation ($Q_s \alpha M^{3/4}$), yields the flow-length relation ($Q_s \alpha L_c$) in the stem-crown unit, which has been previously validated.

Here, the crown length $L_c \alpha M^{3/4}$ is different from the biological length $l \alpha M^{1/4}$. The biological length (l) is the cumulative length along a path from inlet (level zero) to the terminal (level N), but the crown length is the total length of all vessels from inlet to the terminals. Although the biological length shows that the vascular physiology and anatomy are four-dimensional, the crown length depicts a ¾-power relation between the total length of entire/partial biological system and the perfused mass.

Clinical implications of resistance scaling law: The self-similar nature of the structure-function scaling laws in Equations #9, #12 and #13 implies that they can be applied to a partial tree clinically (e.g., a partial tree obtained from an angiogram, computerized tomography, or magnetic resonance imaging). As provided herein, the hypothesis using the LAD, LCx, and RCA epicardial pig trees obtained from casts truncated at 1 mm diameter to mimic the resolution of noninvasive imaging techniques was verified. The good agreement between experiments and theory, as shown in FIG. 8, illustrates that the resistance scaling laws can be applied to partial vascular trees as well as entire trees.

Significance of resistance scaling law: The novel resistance scaling law (Equations #9 and #12) provides a theoretical and physical basis for understanding the hemodynamic resistance of the entire tree (or a subtree) as well as to provide a rational for clinical diagnosis. The scaling law illustrates the relationship between the structure (tree) and function (resistance), in which the crown resistance is proportional to the crown length and inversely proportional to the fourth power of stem diameter $D_s^4$. The small crown resistance corresponds to a small crown length, thus matching the transport efficiency of the crown. An increase of stem diameter can decrease the resistance, which may contribute to the self scaling of biological transport system. The novel scaling law provides an integration between a single unit and the whole (millions of units) and imparts a rationale for diagnosis of disease processes as well as assessment of therapeutic trials.

The disclosure of the present application provides a novel volume scaling law in a vessel segment and its corresponding distal tree of normal organs and in various species as, for example, $V_c = K_v D_s^{2/3} L_c$, where $V_c$ and $L_c$ are the vascular volume and length, respectively, $D_s$ is the diameter of vessel segment, and $K_v$ is a constant. A novel scaling relation of the disclosure of the present application is validated with available vascular morphometric tree data, and may serve as a control reference to examine the change of blood volume in various organs under different states using conventional imaging. A novel scaling law of the disclosure of the present application is further validated through diameter-length, volume-length, flow-diameter, and volume-diameter scaling relations, derived based on a minimum energy hypothesis (15). Hence, the novel volume scaling law of the disclosure of the present application is consistent with a (minimum energy) state of efficient vascular system.

In addition to the foregoing, it is known that $V_c \alpha M$ (M is the mass perfused by the stem-crown unit) from the ¾ allometric scaling law, where $V_c$ is the crown volume (i.e., the sum of all vessel volumes in the crown). Therefore, $V_c$ can be represented as follows:

$$V_c = C_v M^{1/4} M^{3/4} \tag{14}$$

where $C_v$ is a volume-mass constant.

There are two scaling relations: stem diameter-mass relation, $D_s \alpha M^{3/8}$, wherein $D_s$ is the diameter of stem vessel, and crown length-mass relation, $L_c \alpha M^{3/4}$, wherein $L_c$ is the crown length that is defined as the sum of the lengths or substantially all of the lengths of each vessel in the crown).

From $D_s = C_d M^{3/8}$, $L_c = C_l M^{3/4}$, and Equation #14, one may obtain:

$$V_c = C_v M^{1/4} M^{3/4} = C_v \left(\frac{D_s}{C_d}\right)^{2/3} \frac{L_c}{C_l} = K_v D_s^{2/3} L_c \tag{15}$$

where $K_v = C_v / (C_d^{2/3} C_l)$ is a constant. Since Equation #15 is applicable to any stem-crown unit, one may obtain $V_{max} = K_v D_{max}^{2/3} L_{max}$, so that $$K_v = \frac{V_{max}}{D_{max}^{2/3} L_{max}},$$

where $D_{max}$, $L_{max}$, and $V_{max}$ correspond to the most proximal stem diameter, the cumulative vascular length of entire tree, and the cumulative vascular volume of entire tree, respectively. Equation #15 can also be made non-dimensional as:

$$\left(\frac{V_c}{V_{max}}\right) = \left(\frac{D_s}{D_{max}}\right)^{\frac{2}{3}} \left(\frac{L_c}{L_{max}}\right) \tag{16}$$

Morphometry of Vascular Trees. The volume scaling law of the disclosure of the present application is validated in the asymmetric entire coronary arterial tree reconstructed in pig hearts through the growth algorithm based on measured morphometric data. Furthermore, the asymmetric epicardial coronary arterial trees with vessel diameter greater than 1 mm were used to validate the scaling laws in partial vascular trees to mimic the resolution of medical imaging.

Symmetric vascular trees of many organs down to the smallest arterioles were used to verify the proposed structure-function scaling law, which were constructed in the Strahler system, based on the available literature. The arterial and/or venous trees from the various species were obtained as previously referenced herein.

Data Analysis. All scaling relations (i.e., Equations #16 and #29-32) can be represented by a form of the type:

$$Y = A \cdot X^B \quad (17)$$

where X and Y are defined such that A and B should have theoretical values of unity for Equation #16. X and Y are defined as $$\left(\frac{D_s}{D_{max}}\right)^{\frac{2}{3}}\left(\frac{L_c}{L_{max}}\right) \text{ and } \left(\frac{V_c}{V_{max}}\right),$$

respectively. For Equations #29-32, X and Y are defined as $$\left(\frac{L_c}{L_{max}}\right) \text{ and } \left(\frac{D_s}{D_{max}}\right); \left(\frac{L_c}{L_{max}}\right) \text{ and } \left(\frac{V_c}{V_{max}}\right); \text{ and } \left(\frac{D_s}{D_{max}}\right) \text{ and } \left(\frac{Q_s}{Q_{max}}\right); \left(\frac{D_s}{D_{max}}\right) \text{ and } \left(\frac{V_c}{V_{max}}\right);$$

respectively.

A nonlinear regression was then used to calculate A with B constrained to $3/7, 12/7, 2\frac{1}{3},$ and 3 for Equations #29-32, respectively. The nonlinear regression uses the Marquardt-Levenberg algorithm to find the parameter, A, for the variables X and Y to provide the "best fit" between the equation and the data. In Equations #16 and #29-32, the parameter A should have a theoretical value of one.

Results.

Figure 12A:
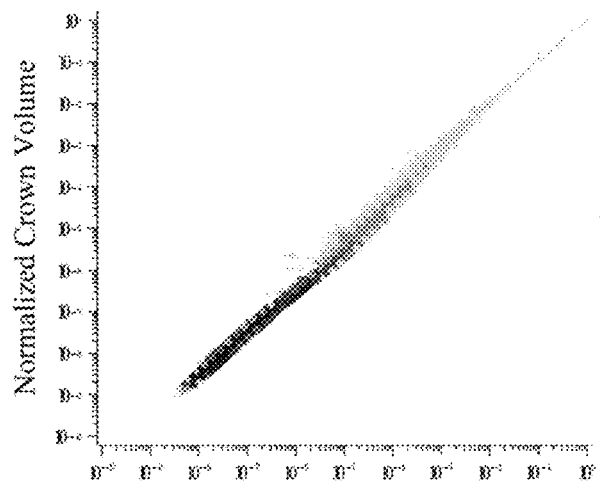
FIGS. 12A-12C show relations between diameter and length and normalized crown volume in the LAD, LCx, and RCA trees of a pig, respectively, according to at least one embodiment of the present disclosure.
Figure 12B:
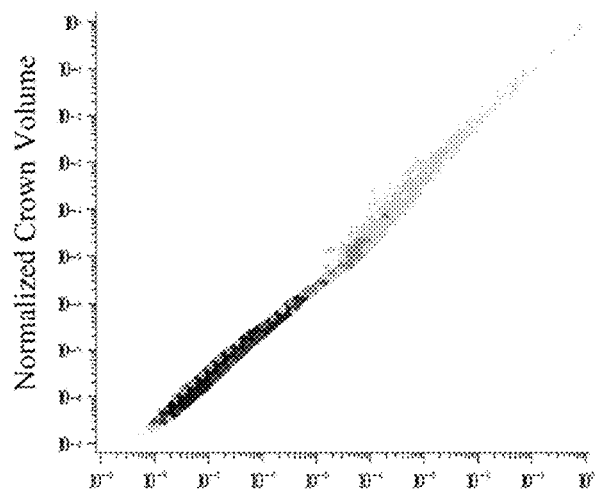
Figure 12C:
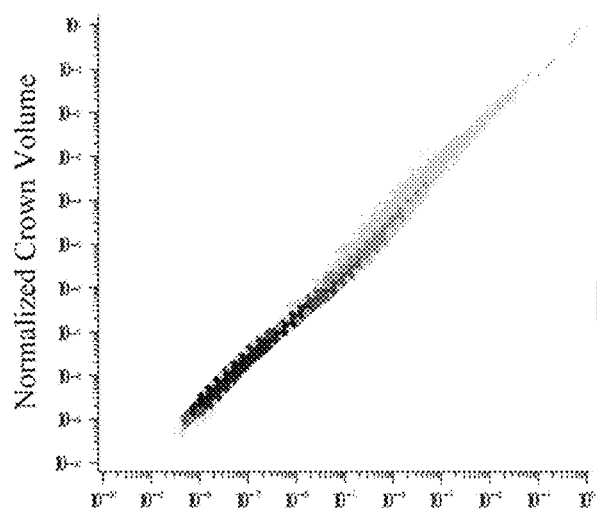
Figure 13:
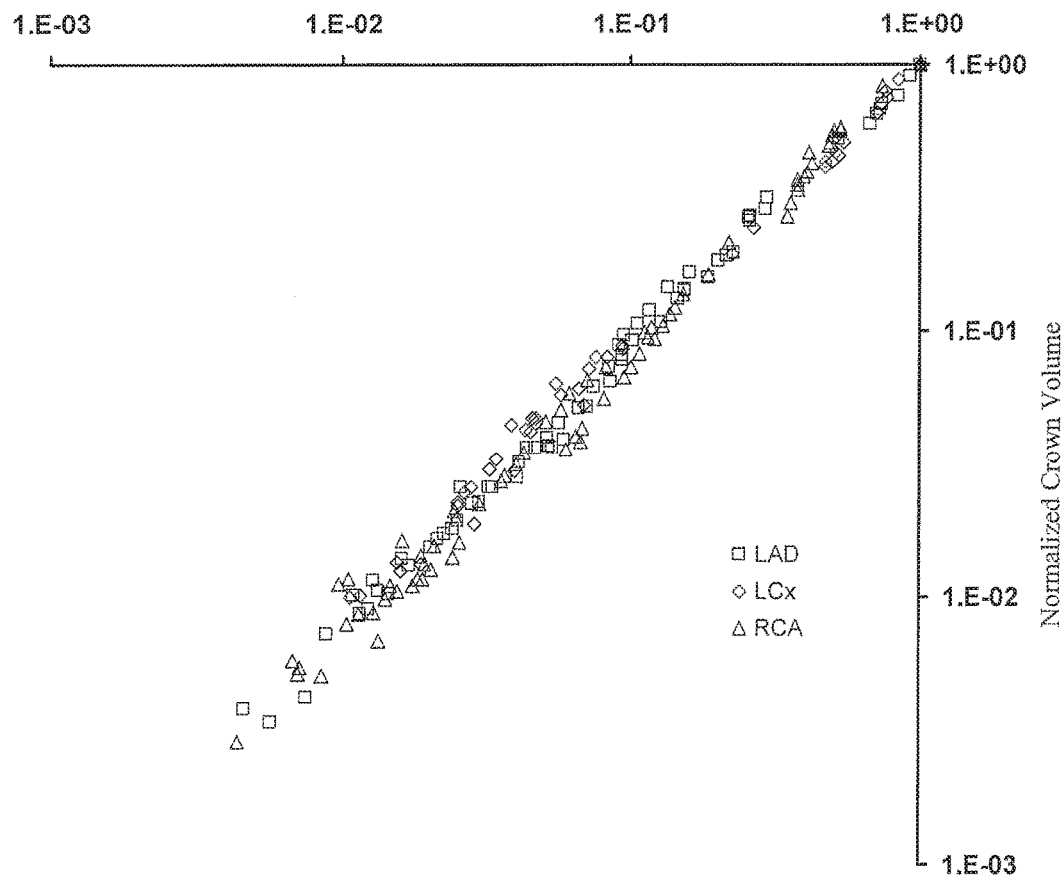
FIG. 13 shows a relation between diameter and length and normalized crown volume in the LAD, LCx, and RCA epicardial trees of a pig, respectively, according to at least one embodiment of the present disclosure.

Asymmetric Tree Model. The disclosure of the present application provides a novel volume scaling law that relates the crown volume to the stem diameter and crown length in Equations #15 and #16. The validity of Equations #15 and #16 were examined in the asymmetric entire (down to the pre-capillary vessel segments) and epicardial (vessel diameter greater than or equal to 1 mm) LAD, LCx, and RCA trees of pig, as shown in FIGS. 12 and 13, respectively. FIG. 12 shows a relation between $$\left(\frac{D_s}{D_{max}}\right)^{\frac{2}{3}}\left(\frac{L_c}{L_{max}}\right)$$

and normalized crown volume in the entire asymmetric (a) LAD, (b) LCx, and (c) RCA trees of pig, which include 946,937, 571,383, and 836,712 vessel segments, respectively. The entire tree data are presented as log-log density plots showing the frequency of data because of the enormity of data points, i.e., darkest shade reflects highest frequency or density and the lightest shade reflects the lowest frequency. FIG. 13 shows a relation between $$\left(\frac{D_s}{D_{max}}\right)^{\frac{2}{3}}\left(\frac{L_c}{L_{max}}\right)$$

and normalized crown volume in the asymmetric LAD, LCx, and RCA epicardial trees of pig with vessel diameter larger than 1 mm, which include 66, 42, and 71 vessel segments, respectively.

As shown in FIG. 9, exponent B is determined from a least-square fit, and parameter A is calculated by the nonlinear regression with the exponent B constrained to one. Both B and A for the entire asymmetric and partial trees show agreement with the theoretical value of one. For the table shown in FIG. 9, Parameters B (obtained from least-square fits) and A (obtained from nonlinear regression with B constrained to one) in the asymmetric entire coronary trees and in the corresponding epicardial trees with vessel diameter >1 mm when Equation #16 is represented by Equation #17, where independent variables $$X = \left(\frac{D_s}{D_{max}}\right)^{\frac{2}{3}}\left(\frac{L_c}{L_{max}}\right) \text{ and } Y = \left(\frac{V_c}{V_{max}}\right),$$

as shown in FIGS. 12 and 13. SE and $R^2$ are the standard error and correlation coefficient, respectively.

Figure 14:
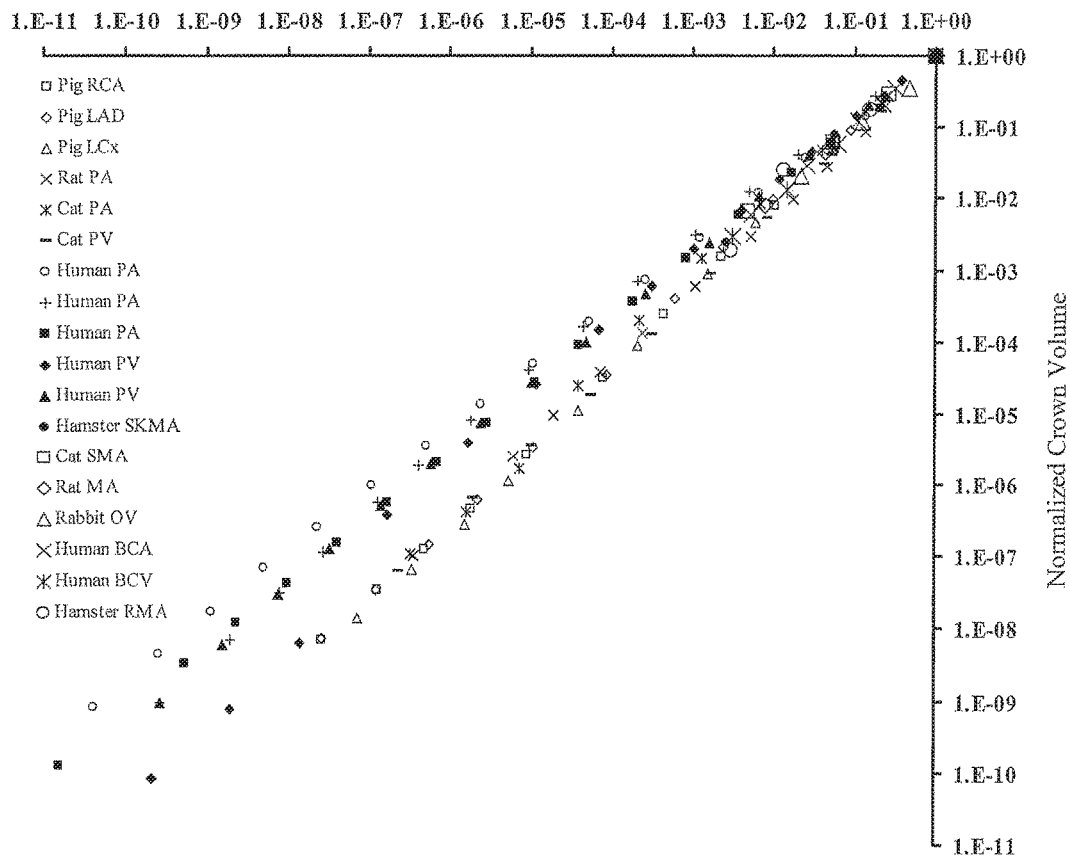
FIG. 14 shows a relation between diameter and length and normalized crown volume in the symmetric vascular tree for various organs and species, according to at least one embodiment of the present disclosure.

Symmetric Tree Model. Equation #16 is also validated in symmetric trees for various organs and species, as shown in FIG. 14. FIG. 14 shows a relation between $$\left(\frac{D_s}{D_{max}}\right)^{\frac{2}{3}}\left(\frac{L_c}{L_{max}}\right)$$

and normalized crown volume in the symmetric vascular tree for various organs and species (21-33), corresponding to the table shown in FIG. 10. Parameters B and A are listed in the table shown in FIG. 10, which have a mean±SD value of 1.02±0.02 and 1.00±0.01, respectively, by averaging over various organs and species. These parameters are in agreement with the theoretical value of one. Furthermore, Equation #15 implies that $$K_v = \frac{V_{max}}{D_{max}^{2/3} L_{max}},$$

which can be compared with the regression-derived value. For the table shown in FIG. 10, parameters B (obtained from least-square fits) and A (obtained from nonlinear regression with B constrained to one) in various organs when Equation #16 is represented by Equation #17, where independent variables $$X = \left(\frac{D_s}{D_{max}}\right)^{\frac{2}{3}}\left(\frac{L_c}{L_{max}}\right) \text{ and } Y = \left(\frac{V_c}{V_{max}}\right),$$

as shown in FIG. 14. SE and $R^2$ are the standard error and correlation coefficient, respectively.

Figure 15:
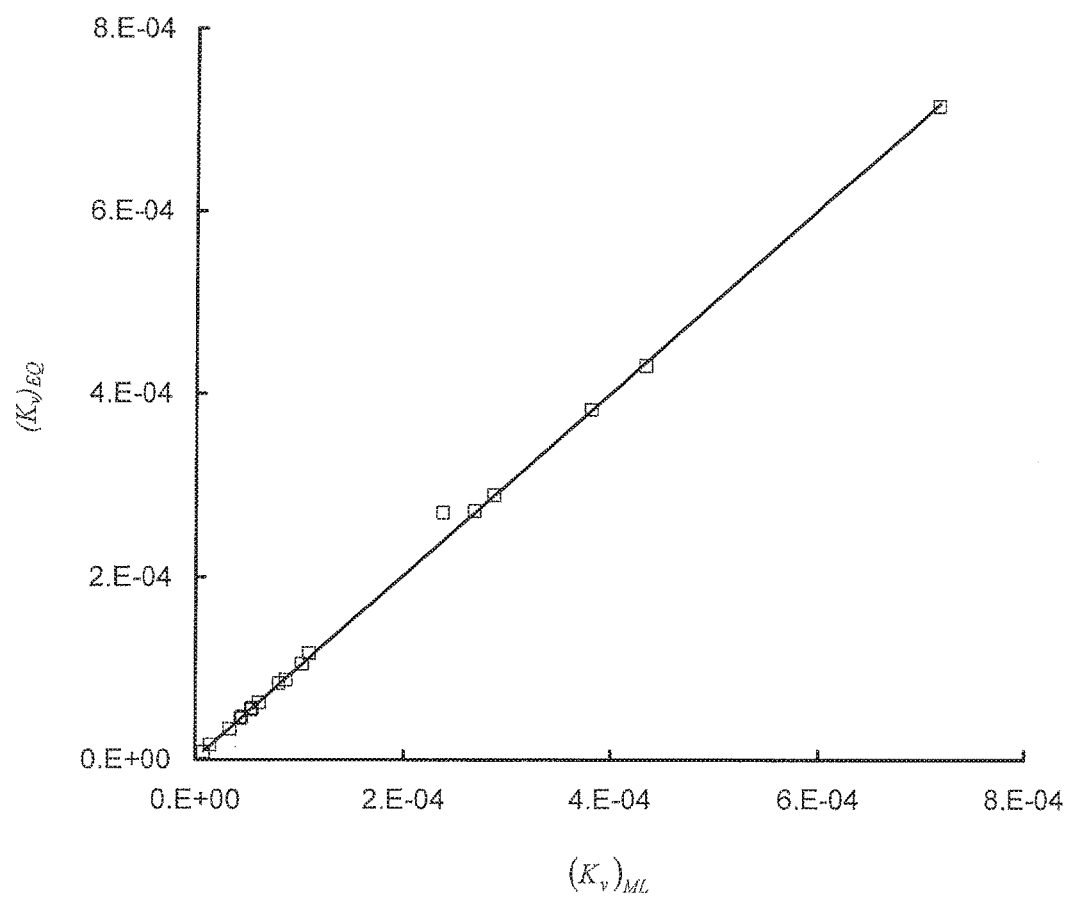
FIG. 15 shows a comparison of data from nonlinear regression and an equation of the present disclosure; according to at least one embodiment of the present disclosure.

FIG. 15 shows a comparison of $(K_v)_{ML}$ obtained from the nonlinear regression of anatomical data and $(K_v)_{EQ}$, calculated from Equations #15 and #16. A least-square fit results in a relation of the form: $(K_v)_{EQ}=0.998(K_v)_{ML}$ ($R^2=0.999$).

Scaling Relations. To further validate the novel volume scaling law of the disclosure of the present application, a number of scaling relations between morphological and hemodynamic parameters are provided below. For these relations, parameter A has the theoretical value of one as exponent B has a theoretical value of $3/7, 12/7, 2\frac{1}{3}$, and 3 for diameter-length relation, volume-length relation, flow-diameter relation, and volume-diameter relation in Equations #29-32, respectively. The values for A are listed in the table shown in FIG. 11 as determined from nonlinear regression. These values, averaged over various organs and species, have mean±SD values of 1.01±0.07, 1.00±0.02, 0.99±0.05, and 0.99±0.03 for Equations #29-32, respectively. The agreement of data with theoretical predictions is excellent as demonstrated by the data referenced herein. For the table shown in FIG. 11, the parameter A obtained from nonlinear regression in various organs when Equations #29-32 (diameter-length, volume-length, flow-diameter, and volume-diameter relations, respectively) are represented by Equation #17. The exponent B is constrained to $3/7, 12/7, 2\frac{1}{3}$, and 3 for Equations #29-32, respectively. SE and $R^2$ are the standard error and correlation coefficient, respectively.

Volume Scaling Law. Many structural and functional features are found to have a power-law (scaling) relation to body size, metabolic rates, etc. Previous studies showed several scaling relations connecting structure with function. A novel volume scaling relation of the disclosure of the present application has been demonstrated and validated, which relates the crown volume to the stem diameter and crown length.

Clinical techniques (e.g., indicator and dye-dilution method) have been used to predict blood volume for decades. The blood volume varies significantly with body size such that it is difficult to evaluate the change of blood volume in patients because of lack of reference. Although Feldschuh and Enson (Prediction of the normal blood volume: relation of blood volume to body habitus. Circulation. 56: 605-612 (1977) used the metropolitan life height and weight tables to determine an ideal weight as an approximate reference, this approach lacks a physical or physiological basis for calculating normal blood volume. The novel volume scaling law of the disclosure of the present application may establish the signature of "normality" and deviation thereof may be indicative of pathology.

The remodeling of intravascular volume may be physiologic during normal growth, exercise, or pregnancy. It may also be pathological, however, in hypertension, tumor, or diffuse vascular diseases. Diffuse vascular disease is difficult to quantify because the normal reference does not exist. The disclosure of the present application shows that the volume scaling law holds in the coronary epicardial trees (vessel diameter >1 mm), as shown in FIG. 13 and the table shown in FIG. 9. Such data on coronaries or other vascular trees are available, for example, by angiography, CT, or MRI. Hence, the novel volume scaling law of the disclosure of the present application can serve to quantify diffuse vascular disease in various organs clinically.

Comparison with ZKM Model. As referenced herein, vascular trees provide the channels to transport fluid to different organs. The optimal design of vascular tree is required to minimize energy losses. Although many theoretical approaches are proposed to explain the design of vascular tree, the "Minimum Energy Hypothesis" may be the most validated hypothesis. The ZKM model, based on the minimum energy hypothesis, predicted the exponents $$\chi = \frac{3\varepsilon'-2}{4(\varepsilon'+1)}, \beta = \frac{5}{\varepsilon'+1}, \delta = \frac{4(\varepsilon'+1)}{3\varepsilon'-2}$$

for diameter-length, volume-length, and flow-diameter relations, respectively, where the parameter ε' in the exponents is the ratio of maximum metabolic to viscous power dissipation for a given tree. Based on Equations #15 and #16 of the disclosure of the present application, the corresponding exponents $\chi=3/7, \beta=12/7,$ and $\delta=2\frac{1}{3}$ are shown. With the respective ε', the mean values over all organs and species are 0.43±0.02, 1.2±0.09, and 2.33±0.11 for exponents χ, β, δ, respectively, which agrees well with the present predicted information, i.e., $3/7 \approx 0.43, 12/7 \approx 1.29,$ and $2\frac{1}{3} \approx 2.33$.

Furthermore, ZKM model shows the mean±SD value of 2.98±0.34 for volume-diameter relation with the respective ε', which is consistent with the exponent value of 3 in Equation #32. This provides further validation for the proposed volume scaling law of the disclosure of the present application.

Comparison with ¾-power Law. West et al. (A general model for the origin of allometric scaling laws in biology. Science. 276:122-126 (1997)) proposed the ¾-power scaling law (WBE model) to describe how essential materials are transported in the vascular tree. The WBE model predicts the following scaling relations: $Q_s \alpha M^{3/4}$, $V_c \alpha M$, and $D_s \alpha M^{3/8}$. If the first and third relations are combined, one obtains the flow-diameter relation with an exponent of Δ=2, which implies that the flow velocity is constant from the large artery to the smallest arterioles. This is in contradiction with experimental measurements.

If the second and third relations are combined, one obtains the volume-diameter relation as:

$$\left(\frac{V_c}{V_{max}}\right) = \left(\frac{D_s}{D_{max}}\right)^{\frac{8}{3}} = \left(\frac{A_s}{A_{max}}\right)^{\frac{4}{3}},$$

such that the area-volume relation is $$\left(\frac{A_s}{A_{max}}\right) = \left(\frac{V_c}{V_{max}}\right)^{\frac{3}{4}},$$

where $A_s$ and $A_{max}$ are the stem area and the most proximal area, respectively. These WBE predictions differ from the experimental observation:

$$\left(\frac{A_s}{A_{max}}\right) = \left(\frac{V_c}{V_{max}}\right)^{\frac{2}{3}}.$$

When the cost function in Equation #22 is minimized, one obtains the exponent δ=2⅓, which agrees well with the anatomical data (as shown in the table of FIG. 10). The area-volume relation $$\left(\left(\frac{A_s}{A_{max}}\right) = \left(\frac{V_c}{V_{max}}\right)^{\frac{2}{3}}\right)$$

obtained from Equation #32 is consistent with the experimental measurements.

There is additional departure of the present model from that of WBE. Equation #30 and $V_c \alpha M$ lead to the following relation:

$$L_c \propto M^{\frac{7}{9}} \quad (18)$$

From Equations #18 and #25, the following relation may be identified:

$$Q_s \propto M^{\frac{7}{9}} \quad (19)$$

From Equation #32 and $V_c \alpha M$, the following relation may be identified:

$$D_s \propto M^{\frac{1}{3}} \quad (20)$$

Although these scaling relations are different from the WBE model, $$V_c \propto D_s^{\frac{2}{3}} L_c$$

(Equations #18 and #20 and $V_c \alpha M$) is still obtained, which further supports the validity of Equations #15 and #16. Equation #19 implies that the ¾-power scaling law ($Q_s \alpha M^{3/4=0.75}$) should be ⅞-power scaling law ($Q_s \alpha M^{7/9=0.78}$). A least-square fit of $Q_s$–M data has an exponent value of 0.78 ($R^2$=0.985), which is consistent with the ⅞-power scaling law.

Optimal Cost Function. From Equations #26 and #28, the non-dimensional cost function can be written as follows:

$$f_c = \frac{1}{6}\frac{(L_c/L_{max})^3}{(D_s/D_{max})^4} + \left(\frac{D_s}{D_{max}}\right)^{2/3}\left(\frac{L_c}{L_{max}}\right) \quad (21)$$

This is the minimum cost of maintaining an optimal design of a vascular tree under homeostasis. From the structure-function scaling relations (Equation #29), $$\frac{(L_c/L_{max})^3}{(D_s/D_{max})^4} = \left(\frac{L_c}{L_{max}}\right)^{1\frac{2}{7}} \text{ and } \left(\frac{D_s}{D_{max}}\right)^{2/3}\left(\frac{L_c}{L_{max}}\right) = \left(\frac{L_c}{L_{max}}\right)^{1\frac{2}{7}},$$

one may obtain $$\frac{(L_c/L_{max})^3}{(D_s/D_{max})^4} = \left(\frac{D_s}{D_{max}}\right)^{2/3}\left(\frac{L_c}{L_{max}}\right).$$

The power required to overcome the viscous drag of blood flow (second term in Equation #21) is one sixth of the power required to maintain the volume of blood (third term in Equation #21). This expression implies that most of energy is dissipated for maintaining the metabolic cost of blood, which is proportional to the metabolic dissipation.

Additional Validation of Volume Scaling Law. From Equations #15 and 16, the disclosure of the present application identifies the cost function for a crown, $F_c$, consistent with previous formulation:

$$F_c = Q_s \cdot \Delta P_c + K_m V_c = Q_s^2 \cdot R_c + K_m K_v D_s^{2/3} L_c \quad (22)$$

where $Q_s$ and $\Delta P_c = Q_s R_c$ are the flow rate through the stem and the pressure drop in the distal crown, respectively, and $K_m$ is a metabolic constant of blood in a crown. The resistance of a crown has been identified as $$R_c = K_c \frac{L_c}{D_s^4},$$

where $K_c$ is a constant. The cost function of a crown tree in Equation #22 can be written as:

$$F_c = Q_s^2 \cdot R_c + K_m K_v D_s^{2/3} L_c = K_c Q_s^2 \frac{L_c}{D_s^4} + K_m K_v D_s^{2/3} L_c \quad (23)$$

Equation #23 can be normalized by the metabolic power requirements of the entire tree of interest, $K_m V_{max} = K_m K_v D_{max}^{2/3} L_{max}$, to obtain:

$$f_c = \frac{F_c}{K_m K_v D_{max}^{2/3} L_{max}} = \quad (24)$$
$$= \frac{Q_{max}^2 R_{max}}{K_m K_v D_{max}^{2/3} L_{max}}\left(\frac{Q_s}{Q_{max}}\right)^2 \cdot \frac{(L_c/L_{max})}{(D_s/D_{max})^4} + \left(\frac{D_s}{D_{max}}\right)^{2/3}$$
$$\left(\frac{L_c}{L_{max}}\right)$$

where $f_c$ is the non-dimensional cost function. A previous analysis shows:

$$Q_s = K_Q L_c \Rightarrow \frac{Q_s}{Q_{max}} = \frac{L_c}{L_{max}} \quad (25)$$

where $K_Q$ is a flow-crown length constant. When Equation #25 is applied to Equation #24, the dimensionless cost function can be written as:

$$f_c = \frac{Q_{max}^2 R_{max}}{K_m K_v D_{max}^{2/3} L_{max}} \cdot \frac{(L_c/L_{max})^3}{(D_s/D_{max})^4} + \left(\frac{D_s}{D_{max}}\right)^{2/3}\left(\frac{L_c}{L_{max}}\right) \quad (26)$$

Similar to Murray's law, the cost function may be minimized with respect to diameter at a fixed $L_c/L_{max}$ to obtain the following:

$$\frac{\partial f_c}{\partial \left(\frac{D_s}{D_{max}}\right)} = 0 \Rightarrow \frac{(-4)Q_{max}^2 R_{max}}{K_m K_v D_{max}^{2/3} L_{max}} \cdot \frac{(L_c/L_{max})^3}{(D_s/D_{max})^5} \qquad (27)$$

$$= -\left(\frac{2}{3}\right)\left(\frac{D_s}{D_{max}}\right)^{\frac{2}{3}-1}\left(\frac{L_c}{L_{max}}\right) \Rightarrow \frac{6Q_{max}^2 R_{max}}{K_m K_v D_{max}^{2/3} L_{max}} \cdot \left(\frac{L_c}{L_{max}}\right)^2$$

$$= \left(\frac{D_s}{D_{max}}\right)^{4+\frac{2}{3}}$$

Equation #27 applies to any stem-crown unit. When $L_c = L_{max}$ and $D_s = D_{max}$ in Equation #27, one may obtain:

$$\frac{6Q_{max}^2 R_{max}}{K_m K_v D_{max}^{2/3} L_{max}} = 1 \Rightarrow \frac{Q_{max}^2 R_{max}}{K_m K_v D_{max}^{2/3} L_{max}} = \frac{1}{6} \qquad (28)$$

Therefore, Equation #28 can be written as:

$$\left(\frac{D_s}{D_{max}}\right) = \left(\frac{L_c}{L_{max}}\right)^{\frac{3}{7}} \qquad (29)$$

From Equations #16 and #29, one may obtain:

$$\left(\frac{V_c}{V_{max}}\right) = \left(\frac{L_c}{L_{max}}\right)^{1\frac{2}{7}} \qquad (30)$$

From Equations #25 and #29, one may find:

$$\left(\frac{Q_s}{Q_{max}}\right) = \left(\frac{D_s}{D_{max}}\right)^{2\frac{1}{3}} \qquad (31)$$

where $Q_{max}$ is the flow rate through the most proximal stem. From Equations #29 and #30, one may obtain:

$$\left(\frac{V_c}{V_{max}}\right) = \left(\frac{D_s}{D_{max}}\right)^3 \qquad (32)$$

Equations #29-32 are the structure-function scaling relations in the vascular tree, based on the "Minimum Energy Hypothesis". Equations #29, #30, and #32 represent the diameter-length, volume-length, and volume-diameter relations, respectively and Equation #31 represents the general Murray's law in the entire tree.

The disclosure of the present application also relates to the design and fabrication of micro-fluidic chambers for use in research and development, thereby designing a chamber that maximizes flow conditions while minimizing the amount of material needed to construct the chamber. Many other uses are also possible and within the scope of the disclosure of the present application.

In addition to the foregoing, various models that express the relation of the diameters of the three segments of a bifurcation have been proposed to determine the optimal diameter of the third diseased segment. Murray (The Physiological Principle of Minimum Work: I. The Vascular System and the Cost of Blood Volume. Proc. Natl. Acad. Sci. U.S.A. 12, 207-214 (1926)) was the first to derive a cubed relationship between the mother and two daughter vessels. The premise of Murray's derivation is the minimum energy hypothesis; i.e., the energy rate for transport of blood through the bifurcation is minimized. This is the principle of efficiency, where departure from which requires greater energy dissipation. Huo and Kassab (A scaling law of vascular volume. Biophys. J 96, 347-353 (2009)) recently showed a similar relationship based on the same premise, but with an exponent of 2⅓. Finet et al. (Fractal geometry of arterial coronary bifurcations: a quantitative coronary angiography and intravascular ultrasound analysis. EuroIntervention 3, 490-498 (2008)) proposed an empirical fractal-like rule. An additional expression based on area conservation has traditionally been invoked for the vasculature (Kamiya, A. & Togawa, T. Optimal branching structure of the vascular tree. Bull Math Biophys 34, 431-438 (1972)).

FIG. 16 shows the most commonly referenced bifurcation models that provide a mathematical relation between the three segments of a bifurcation. The mathematical forms and physical mechanisms for the HK, Murray, area-preservation, and Finet models are listed in FIG. 16. The diameters of mother, larger and smaller daughter bifurcation segments are represented by $D_m$, $D_l$ and $D_s$, respectively.

Figure 17A:
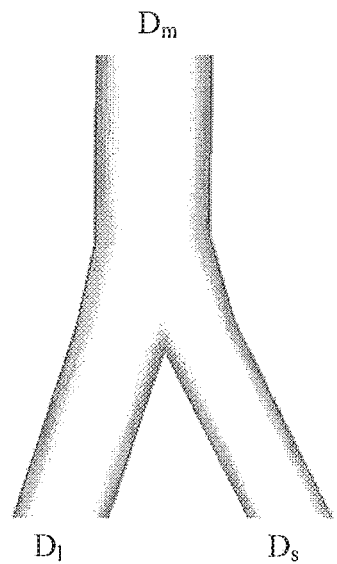
FIGS. 17A and 17B show schematic representations of Y and T vessel bifurcations, according to embodiments of the present disclosure.
Figure 17B:
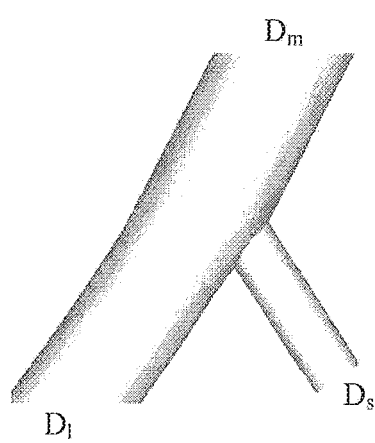

FIGS. 17A and 17B show the two types of vessel bifurcations. FIG. 17A shows a Y-type bifurcation, and FIG. 17B shows a T-type bifurcation. The ratio of the smaller to larger daughter bifurcation segments $D_s/D_l$ is assumed to have values of 0.75 to 1 for Y-type bifurcations and 0.25 to 0 for T-type bifurcations. $D_s$ represents the diameter of the smaller daughter bifurcation and $D_l$ represents the diameter of the larger daughter bifurcation. The accuracy of the Murray, Finet, area-preservation and HK models were compared for both Y and T bifurcations.

The disclosure of the present application determines the ratio $$\frac{D_m}{D_l + D_s}$$

as a function of the daughter diameter ratio based on the Murray, Finet, area-preservation and HK models shown in FIG. 16. $D_m$ represents the diameter of the mother bifurcation segment. Equation #33 demonstrates a relationship between $$\frac{D_m}{D_l + D_s}$$

and the HK model:

$$1 + \frac{D_s}{D_o} \downarrow$$

Equation #34 demonstrates a relationship between $$\frac{D_m}{D_l + D_s}$$

and the Murray model:

$$\begin{cases} \dfrac{D_m}{D_l+D_s}\sqrt[3]{\dfrac{D_m^3}{(D_l+D_s)^3}} \Rightarrow \dfrac{D_m}{D_l+D_s}=\sqrt[3]{\dfrac{D_l^3+D_s^3}{(D_l+D_s)^3}}=\sqrt[3]{\dfrac{1+\left(\dfrac{D_s}{D_l}\right)^3}{1+\left(\dfrac{D_s}{D_l}\right)^3}} \\ D_m^3=D_l^3+D_s^3 \end{cases} \quad (33)$$

Equation #35 demonstrates a relationship between $$\dfrac{D_m}{D_l+D_s}$$

and the area-preservation model:

$$\begin{cases} \dfrac{D_m}{D_l+D_s}\sqrt{\dfrac{D_m^2}{(D_l+D_s)^2}} \Rightarrow \dfrac{D_m}{D_l+D_s}=\sqrt[3]{\dfrac{D_l^2+D_s^2}{(D_l+D_s)^2}}=\sqrt[3]{\dfrac{1+\left(\dfrac{D_s}{D_l}\right)^2}{1+\left(\dfrac{D_s}{D_l}\right)^2}} \\ D_m^2=D_l^3+D_s^2 \end{cases} \quad (34)$$

Equation #36 demonstrates a relationship between $$\dfrac{D_m}{D_l+D_s}$$

and the Finet model:

$$\dfrac{D_m}{D_l+D_s}=0.678 \quad (35)$$

Equations #33-36 represent the ratio $$\dfrac{D_m}{D_l+D_s}$$

as a function of the daughter diameter ratio $D_s/D_l$ derived from the HK, Murray, area-preservation, and Finet models, respectively. As the daughter diameter ratio approaches 1 in Y-bifurcations, Equations #33-36 give 0.673, 0.63, 0.707, and 0.678 for the HK, Murray, area-preservation, and Finet models, respectively. As the daughter diameter ratio approaches 0 in T-bifurcations, Equations #33-36 give 1 for the HK, Murray, area-preservation models and 0.678 for Finet model.

Figure 18:
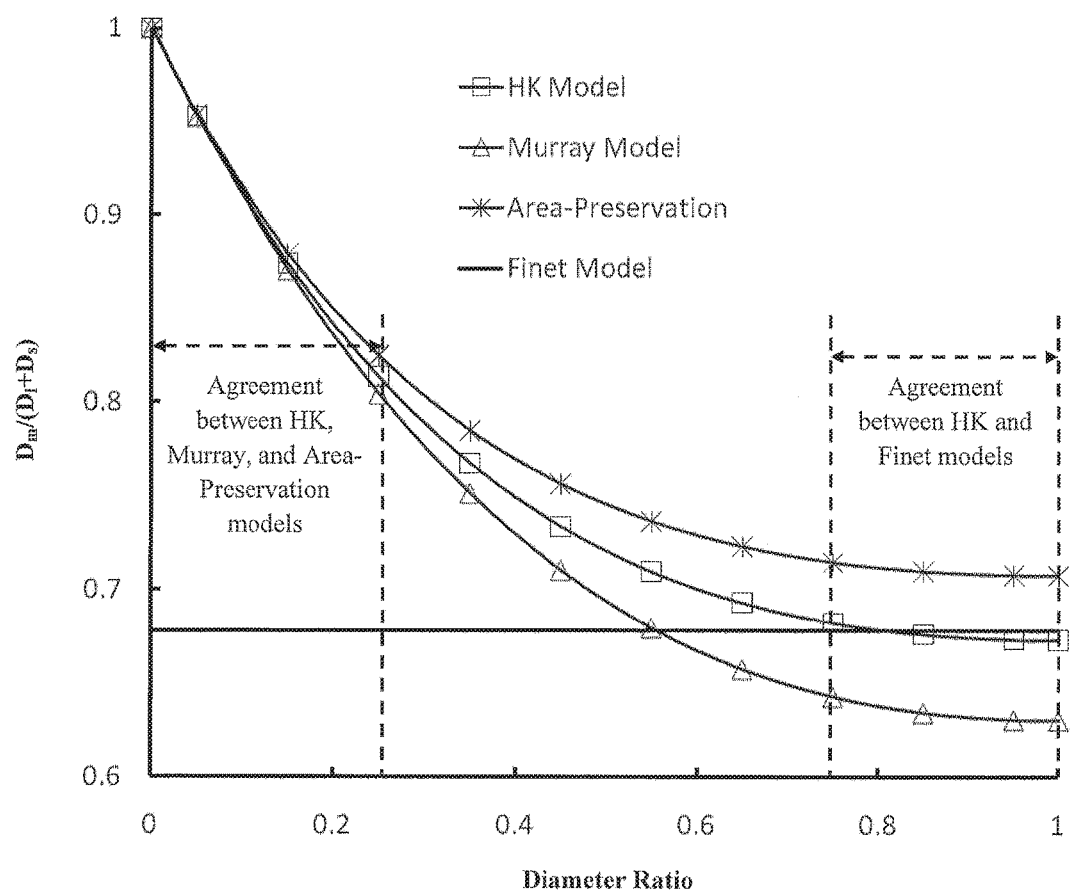
FIG. 18 shows a relationship between $D_m/(D_l+D_s)$ and diameter ratio $(D_s/D_l)$ determined by the HK, Finet, Muray and area-preservation models, according to an embodiment of the present disclosure.

FIG. 18 shows the relationship between $$\dfrac{D_m}{D_l+D_s}$$

and diameter ratio $D_s/D_l$ determined from bifurcation diameter models in Equations #33-36. FIG. 19 shows values of $$\dfrac{D_m}{D_l+D_s}$$

in Y-bifurcations $D_s/(D_l$ varying from 0.75 to 1) and T-bifurcations $D_s/(D_l$ varying from 0.25 to 0) as determined by the Murray, Finet, area-preservation, and HK models (i.e., Equations #33-35 respectively). Only the HK model shows good agreement with the Finet model in Y-type bifurcation (i.e. 0.676 vs. 0.678).

FIG. 20 shows the values of relative error between the bifurcation diameter models in FIG. 16 and measurements of quantitative coronary bifurcation angiography in Finet et al. (Fractal geometry of arterial coronary bifurcations: a quantitative coronary angiography and intravascular ultrasound analysis. EuroIntervention 3, 490-498 (2008)).

FIG. 21 shows the values of relative error between the bifurcation diameter models and experimental results in the left anterior descending artery (LAD) tree of a porcine heart with mother diameters ≥0.5 mm obtained from casts in Kassab et al. (Morphometry of pig coronary arterial trees. Am. J. Physiol 265, H350-365 (1993)). The values of error for the four bifurcation models in FIGS. 20 and 21 can be represented as follows:

$$\% \text{Error}_{HK}=\dfrac{\left(D_1^{2\frac{1}{3}}+D_s^{2\frac{1}{3}}-D_m^{2\frac{1}{3}}\right)}{D_m^{2\frac{1}{3}}}\times 100\% \quad (37)$$

$$\% \text{Error}_{Finet}=\dfrac{[(D_1+D_s)\cdot 0.678\cdot D_m]}{D_m}\times 100\% \quad (38)$$

$$\% \text{Error}_{Murray}=\dfrac{(D_1^3+D_s^3-D_m^3)}{D_m^3}\times 100 \quad (39)$$

$$\% \text{Error}_{AP}=\dfrac{(D_1^2+D_s^2-D_m^2)}{D_m^2}\times 100\% \quad (40)$$

wherein Equation #37 represents the percentage of error in the HK model, Equation #38 represents the percentage of error in the Finet model, Equation #39 represents the percentage of error in the Murray model and Equation #40 represents the percentage of error in the area-preservation model. The * symbol in FIG. 21 represents the significant difference (P<0.05) between the HK model and the corresponding model (i.e., Finet, Murray, and area-preservation models), and "n" represents the number of measurements. The values of FIG. 21 are further illustrated in FIG. 22. Only the prediction of the HK model came within ±5% error of the actual experimental values throughout the range of bifurcations.

Finet et al. have empirically shown that the ratio of a mother vessel diameter to the sum of the two daughter-vessel diameters $$\dfrac{D_m}{(D_1+D_s)}$$

is 0.678, based on quantitative coronary angiography and intravascular ultrasound measurements. The Finet model agreed with the experimental measurements of Y-bifurcations much better than the Murray and area-preservation models. As shown in FIG. 20, the HK model agreed well with the experimental measurements of the Finet model despite a relatively small error (<10%) for mother vessel diameter <3 mm. This is likely caused by an increase of experimental error as the vessel diameter decreases, and suggests a relationship between the Finet and HK models.

Equations #33-36 represent the relationships between the four models in FIG. 16. The daughter diameter ratio $$\frac{D_s}{D_l} \to 1 \text{ or } \frac{D_s}{D_l} \to 0$$

correspond to Y- and T-bifurcations respectively, which leads to different values of $$\frac{D_m}{D_l + D_s}.$$

From the HK model, the ratio $$\frac{D_m}{D_l + D_s}$$

in Y-type bifurcations equals to 0.676, which is very similar to 0.678 of the Finet model as shown in FIG. 18 and FIG. 19. From the study of Finet et al., the diameter ratio $$\frac{D_s}{(D_l)}$$

was 0.828±0.024 so that the HK model is consistent with the empirical Finet model, as shown in FIG. 20. However, FIG. 18 shows that the ratio $$\frac{D_m}{D_l + D_s}$$

determined by Equation #33 deviates from the prediction of the Finet model as the daughter diameter ratio decreases away from 0.75. In particular, the values of $$\frac{D_m}{D_l + D_s}$$

determined by the HK, Murray, and area-preservation models are very similar as the daughter diameter ratio decreases monotonically from 0.25 to zero in T-type bifurcations. Accordingly, FIG. 19 shows the increase of $$\frac{D_m}{D_l + D_s}$$

from about 0.8 to unity, which is significantly larger than the prediction of the Finet model. Hence, the Finet model is in gross error for T-type bifurcations.

Figure 22:
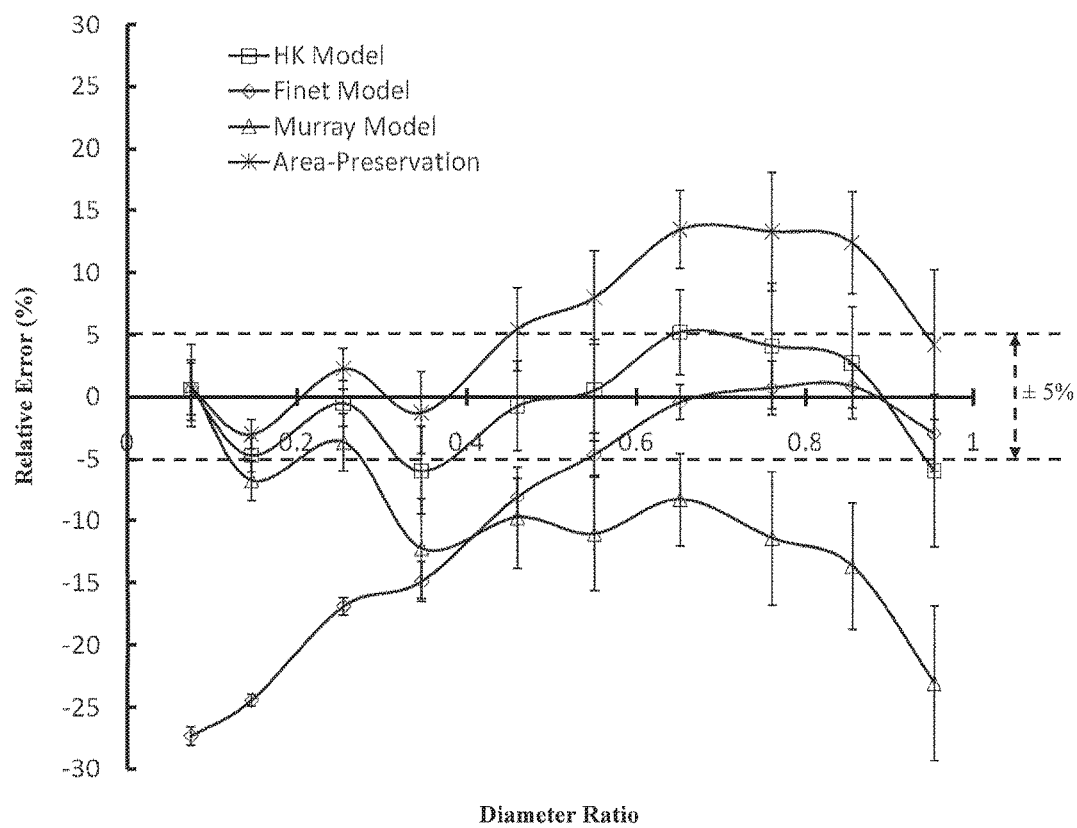
FIG. 22 shows a representation of relative error between bifurcation diameter models and experimental measurements as a function of diameter ratio $(D_s/D_l)$, according to an embodiment of the present disclosure.

Similarly, the four models in FIG. 16 were evaluated using cast data of porcine epicardial coronary bifurcations, as shown in FIGS. 21 and 22. The HK model agrees well with the measurements for all diameter ratios (±5% error); the Murray and area-preservation models agree with the measurements when $D_s/D_l$ is less than or equal to 0.25, and the Finet model agrees with the measurements when $D_s/D_l$ is greater than or equal to 0.65, but not for other diameter ratios.

A comparison of the four bifurcation models shows that the HK model agrees with measurements of all daughter diameter ratios and bifurcation types (e.g., Y and T). The HK model is based on the minimum energy hypothesis and agrees with both Y and T bifurcations, while the Murray and area-preservation models are in agreement with experimental measurements for only T-type bifurcations. The Finet model is empirical and is in agreement for only Y-type bifurcations. The HK model provides the best rule for the percutaneous reconstruction of the diameters of diseased vessels and has a physiological and physical basis. The HK model accurately predicts the optimal diameter of a third diseased segment from the diameters of two known bifurcation segments.

The techniques disclosed herein have tremendous application in a large number of technologies. For example, a software program or hardware device may be developed to determine the optimal diameter of a bifurcation segment.

Regarding the computer-assisted determination of such features, an exemplary system of the disclosure of the present application is provided. Referring back to FIG. 3, there is shown a diagrammatic view of an embodiment of diagnostic system 300 including an exemplary user system 302 of the present disclosure. Diagnostic system 300 and/or user system 302 of the present disclosure may comprise some, most, or all of the components of an exemplary data computation system 800 of the present disclosure, as shown in FIG. 3.

FIG. 23 shows an exemplary embodiment of how the validated HK model can be translated into clinical practice using data computation system 800. A website, handheld device application, or the like may be prepared to allow the determination of a diameter of any of the three segments of a bifurcation if two of the diameters are entered, as outlined in FIG. 23. There is an entry blank for each segment. Once two of the entries are input, one can click the "Calculate" button to yield the third segment consistent with the HK model. This website or application can be downloaded to a mobile phone or other portable device, for example, for a quick and easy rule to determine the reference diameter of a bifurcation for the sizing of balloons or stents.

Figure 24A:
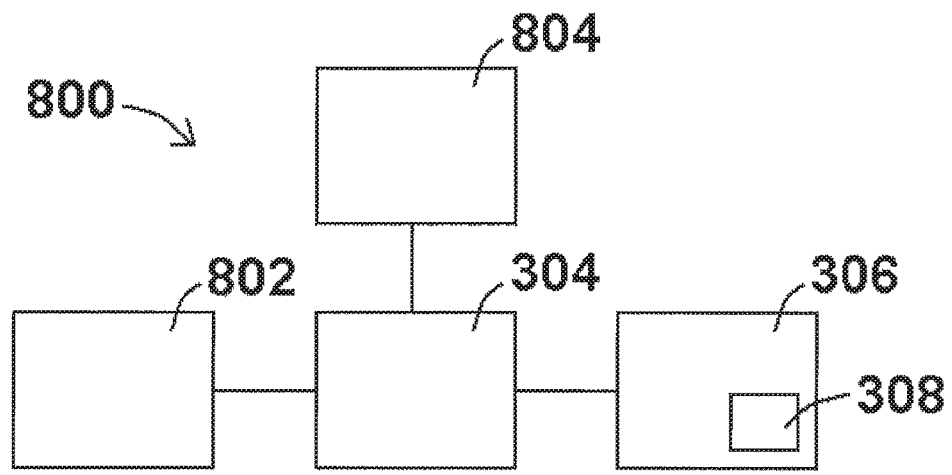
FIG. 24A shows a data computation system according to at least one embodiment of the present disclosure.
Figure 24B:
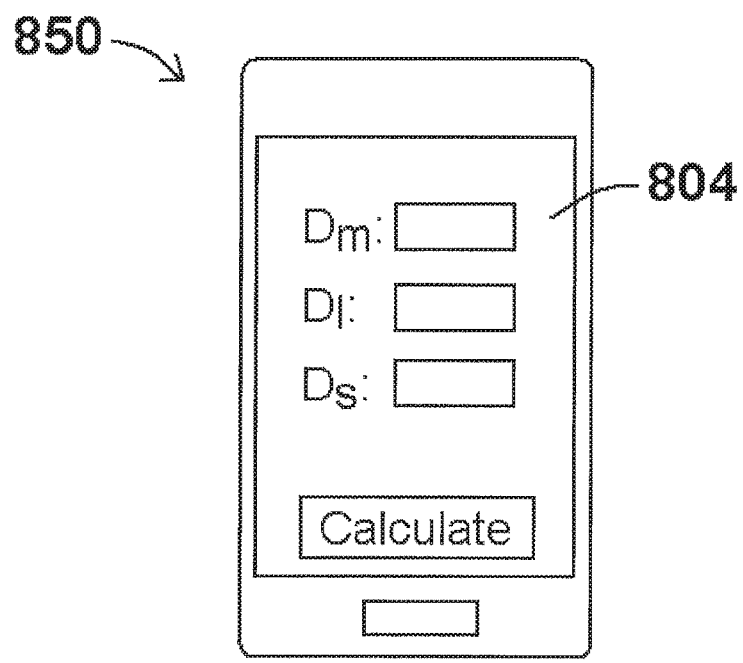
FIG. 24B shows an exemplary data computation device according to at least one embodiment of the present disclosure.

FIG. 24A shows another exemplary embodiment of a data computation system 800 of the present disclosure. As shown in FIG. 24A, exemplary data computation system 800 comprises a processor 304 operably coupled to a storage medium 306 having a program 308 stored thereon. A user interface 802 operably coupled to processor 304 is capable of receiving data indicative of vessel segments, and a display 804 operably coupled to processor 304 is capable of displaying vessel segment data. Components of various data computation systems 800 of the present disclosure may be contained within, or otherwise part of, computation device 850, such as shown in FIG. 24B. Various computation devices 850 may include, but are not limited to, a desktop computer, a laptop computer, a tablet computer, a portable digital assistant, or a smartphone.

Figure 25:
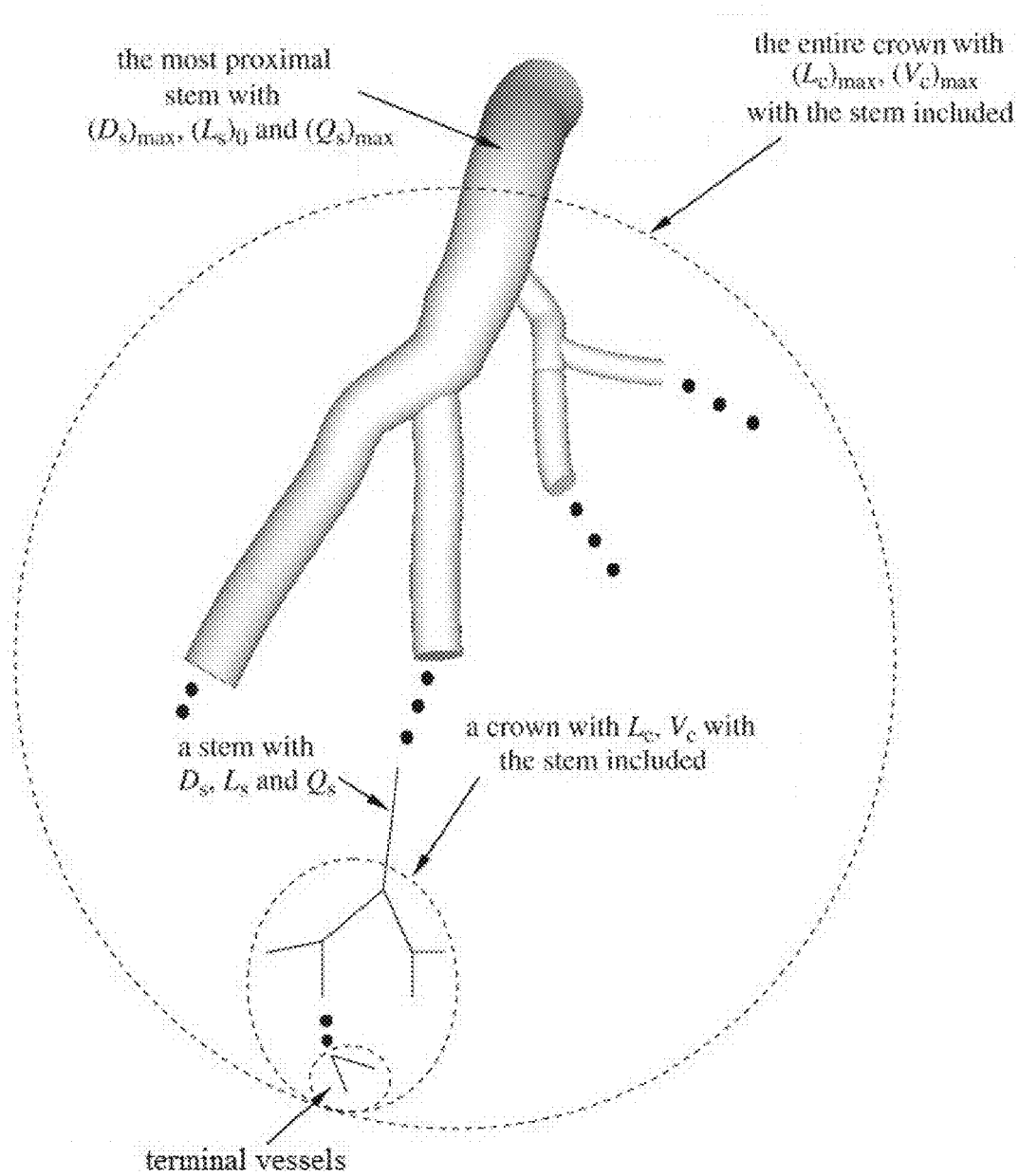
FIG. 25 shows an illustration of a definition of a stem-crown unit and corresponding parameters according to at least one embodiment of the present disclosure, with D, L, Q, and V representing the diameter, length, flow rate, and volume, respectively, subscriptions "s" and "c" corresponding to stem and crown, respectively, in a single stem-crown unit, and the subscript "max" representing the most proximal stem-crown unit in a vascular tree.

The simple, noninvasive and accurate determination of vascular information using the computations disclosed herein has widespread and important practical application. One such application is determining mean transit time to transport blood, oxygen, nutrients, hormones, and cellular waste within the vasculature. To facilitate discussion and understanding of this application, and as with other embodiments disclosed herein, FIG. 25 provides an explanatory illustration regarding the various terms used in the following disclosure. Namely, the term "stem" means a vessel segment and the term "crown" means the vascular tree supplied by the stem. Additionally, in a stem-crown system, the volume of a crown ($V_c$) is defined as the sum of the intravascular volume of the vessel segments ($V_s$) in the entire stem-crown system from the most proximal vessels to the pre-capillary vessels. Similarly, the crown length ($L_c$) is defined as the cumulative vascular lengths ($L_s$) in the entire crown.

As previously stated, at least one application of the foregoing systems and methods for determining morphometric parameters can be used in conjunction with the novel intraspecific scaling laws described herein to accurately and noninvasively determine mean transit time in vascular trees (however, it will be appreciated that the morphometric parameters used with the novel scaling laws relating to mean transit time described herein can be determined in any manner and are not necessarily limited to noninvasive means). In addition to anatomical information regarding the vasculature, information about blood flow is necessary to gain a comprehensive understanding of the functional significance of vascular morphometric data and to evaluate the result of an intervention. However, accurately determining mean transit time (MTT) through specific vasculature can be complicated because, at least in part, the structural heterogeneity of vascular networks and, thus, resulting heterogeneous perfusion, necessarily causes particles within the vasculature to concurrently traverse various paths. Indeed, the MTT is the average time required for all particles to travel through the network over a period of time.

Transit time is critical in providing nutrients to the cells and removing waste products therefrom. It is also very important for drug, cell, and gene delivery. An elementary derivation of the novel scaling laws hereof shows that the ratio of mean transit time in vessel segment and crown ($T_s/T_c$) and the ratio of blood volume in the same vessel segment and corresponding crown ($V_s/V_c$) has a highly significant direct relation ($T_s/T_c=V_s/V_c$; $R^2=1$). Importantly, this novel scaling law has been found to hold true across all organs (e.g., heart, lung, mesentery, skeletal muscle, and eye), species (e.g., rats, cats, rabbits, pigs, hamsters, and humans), and throughout the range of vascular dimensions (from μm to cm) for which morphometric data exists. Furthermore, if the transit time is determined in an organ or tissue based on the approaches disclosed herein, then a constant k can be calculated (see Equation #45 below) based only on the length and volume of the vasculature (which can easily be measured using current x-ray systems or otherwise). Accordingly, the transit time can be determined for any portion of the vasculature dictated by its volume and length. Beyond vascular trees, the methods and techniques disclosed herein also have application to microfluidic channels and other engineered networks for transport. To facilitate the understanding of the present disclosure, the scaling laws hereof will first be described generally, followed by a more detailed description of the methods, materials, and computations used to validate the same.

Based on the assumption that the total number of particles that pass through a segment is proportional to the time-averaged flow rate in the segment, the MTT in a network ($T_c$) can be written as:

$$T_c = \sum_{i=1}^{n} (FF)_i \times T_{s,i} \tag{41}$$

where FF is the flow fraction (ratio of time-averaged flow rate of the segment to the time-averaged flow rate of the proximal segment); $T_s$ is mean transit time in a specific segment where i=1, 2, ..., n; and n is the total number of segments in the entire network.

Conventionally, it is known that blood volume is a function of blood flow and transit time. As shown in this disclosure, the volume of a segment vessel ($V_s$) is equivalent to discharged volume of fluid into the segment and is related to transit time as:

$$V_s = T_s \times \overline{Q}_s \tag{42}$$

where $\overline{Q}_s$ is time-averaged flow rate over transit time in the segment. Similarly, the cumulative intravascular volume of the entire network $$\left( V_c = \sum_{i=1}^{n} (V_s)_i \right)$$

is the product of the summation of the MTT in the entire network ($T_s$) and the total time-averaged circulating flow ($\overline{Q}_c$) in the entire network. Hence, the volume of the entire network is written as:

$$V_c = T_c \times \overline{Q}_c \tag{43}$$

(see Examples and Validation for derivation).

As set forth in the Examples below, the combination of Equations #42-43 leads to the conclusion that the time-averaged flow rate of the proximal segment over $T_s$ (e.g., flow of aorta) is equal to the time-averaged flow rate of the entire network segment over $T_c$ (e.g., total flow within the aorta segment plus the distal network). Accordingly, a relationship between transit time in the proximal segment and mean transit time in the entire network can be deduced as:

$$\frac{T_s}{T_c} = \frac{V_s}{V_c} \tag{44}$$

Figure 26:
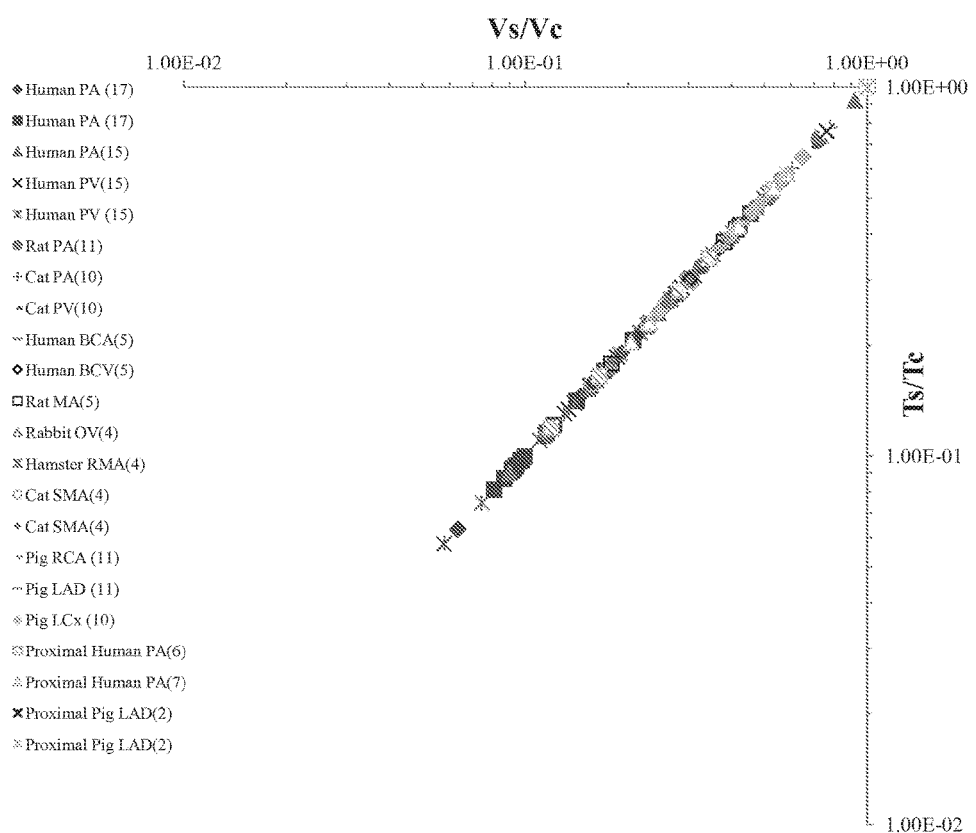
FIG. 26 shows the relation between $(V_s/V_c)$ and $(T_s/T_c)$ in vascular trees of various organs and species for both full and proximal trees according to at least one embodiment of the present disclosure, where a linear relationship is observed, consistent with Eq. (44) (RCA, right coronary artery; LAD, left anterior descending artery; LCx, left circumflex artery; PA, pulmonary artery; PV, pulmonary vein; SMA, sartorius muscle arteries; MA, mesentery arteries; OV, omentum veins; BCA, bulbular conjunctiva arteries; RMA, retractor muscle artery)

The comparison of the two ratios, $T_s/T_c$ and $V_s/V_c$, for both full trees (i.e. down to pre-capillary vessels) and proximal trees (i.e. down to about 1 mm diameter vessels as visualized by standard clinical x-ray methods) is illustrated in FIG. 26. FIG. 26 shows an excellent agreement between Equation #44 and the experimental data. As shown in Table 1, the ratio of transit time in vessel segment and crown ($T_s/T_c$) and the ratio of segment volume and the crown volume of ($V_s/V_c$) display a very significant linear relationship; the proportionality constant is equal to 1 (see Examples and Validation below for details regarding the analysis thereof and related morphometric data). The linear relationship between the ratios indicates that the time required for blood to pass through the proximal vessel segment is proportional to the volume that the stem contributes to the entire volume of vascular network.

Equation #44 does not strictly follow from the Eulerian mass conservation that states flow at inlet of a network is equal to sum of flows at outlets of the network; instead, the basic definition of flow rate (Q=dV/dt) was utilized to deduce Equations #42-44. In light of this, energy minimization and/or optimization principles were not invoked in the derivation. Accordingly, Equation #44 is general and independent of the exact network topology (e.g, fractality, symmetry or asymmetry, presence or absence of collaterals or interconnections) or flow behavior (e.g., laminar, turbulence, recirculation) present within the vasculature of interest.

Interestingly, it has been established that flow scales with cumulative vascular length ($L_c$) of the entire network. Using this flow scaling law in conjunction with Equation #43, a structure-function relation of the MTT in the vascular network can be written as:

$$V_c = k(T_c \times L_c) \quad (45)$$

where parameter k is a proportionality constant in units of area/time. Equation #45 illustrates that the ratio between crown volume and length determines the transit time in a simple analytical expression. This supports that the more vascular volume in a network, the longer time is needed to transport blood, while the more vascular length in a network, the less time is needed for transport.

In application, the transit time in the crown ($T_c$) that is calculated using Equation #44 can be used in Equation #45 to calculate constant k based only on the length and volume of the vasculature of interest (which can be easily measured using current x-ray systems or otherwise). After constant k is determined, Equation #45 can be used to determine an accurate transit time for any portion of the vasculature dictated only by its volume and length.

Figure 27:
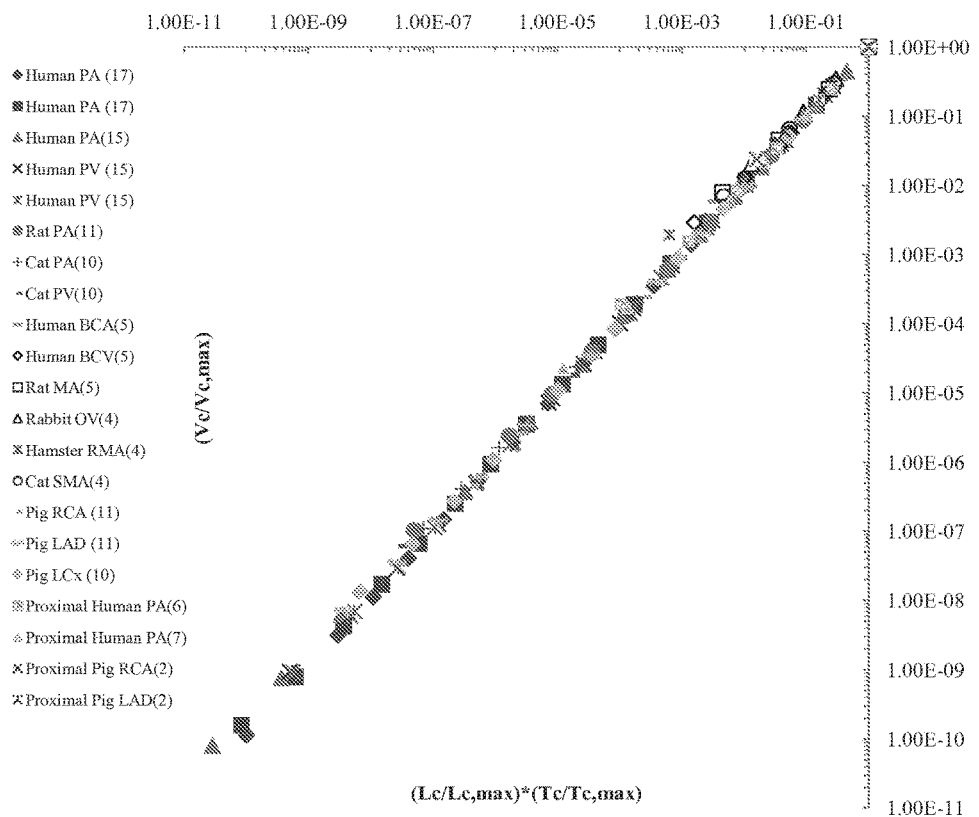
FIG. 27 shows the relation between normalized intravascular volume $(V_c/V_{c,max})$ and normalized multiplication of cumulative vascular length and the mean transit time $(T_c/T_{c,max})(L_c/L_{c,max})$ in the vascular trees of various organs and species as expressed by Eq. (45) according to at least one embodiment of the present disclosure, where the subscript "max" denotes the maximum quantities for the entire crown or tree.

The validity of Equation #45 was tested against experimental data on lengths and volumes, with the maximum quantities in the entire system used to normalize Equation #45. As shown in FIG. 27, the agreement was excellent for vascular trees of various organs in various species (see Table 1).

Figure 28:
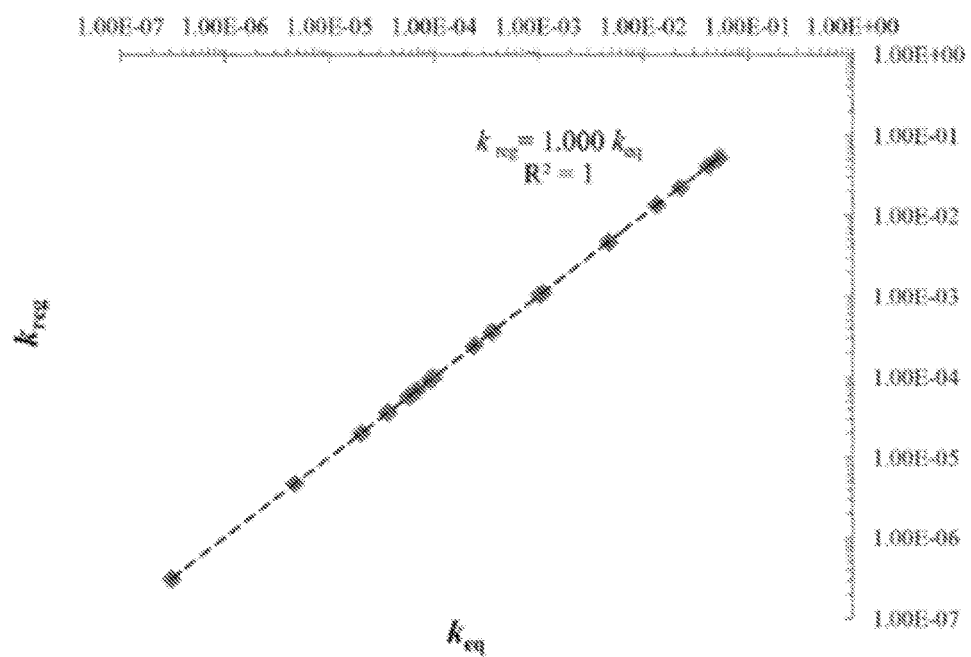
FIG. 28 shows a comparison parameter k in Eq. (45) according to at least one embodiment of the present disclosure, parameter k obtained from the nonlinear regression $k_{reg}$ (see Table 1) and from analytical relation $k_{eq}$, and parameter $k_{eq}$ obtained from Eq. (45), $k_{eq}=(V_{c,max})/((T_{c,max})(L_{c,max}))$; the comparison can be represented as $(k_{reg})=1.000 (k_{eq})$, $R^2=1$.

The predicted values of parameter k from regression between $V_c$ and $T_c \times L_c$ in vascular trees of various organs in various species are listed in Table 1. The correlation between $V_c$ and $T_c \times L_c$ in stem-crown units of vascular tree in various specific organs and species was found to be extremely significant ($0.994 \leq R^2 \leq 1.000$), thus supporting that parameter k has a constant value in an integrated stem-crown system. The conformity of predicted values of parameter k from linear regression ($k_{reg}$) is shown in Table 1 and, as shown in FIG. 28, as compared to analytical values obtained from Equation #45 for maximum quantities in the entire network, $k_{eq} = (V_{c,max})/(T_{c,max} \times L_{c,max})$. The comparison illustrates an excellent agreement, $k_{reg} = 1.000 k_{eq}$ ($R^2 = 1$), which confirms that, although parameter k may vary for vascular trees from organ to organ, it has a constant value in an integrated stem-crown system of a particular organ.

TABLE 1

The validation of scaling laws of transit time using general form of scaling laws: $Y = A' X^B$, where theoretical values of parameters A and B are equal to 1. For the validation of Eq. #44 parameters X and Y are defined as $X = (V_s/V_c)$ and $Y = (T_s/T_c)$, as shown in FIG. 26; parameter A and B were obtained from nonlinear regression with B and A constrained to 1, respectively. Similarly, for the validation of Eq. #45, X and Y are defined as $X = (V_c/V_{c,max})(L_{c,max}/L_c)$ and $Y = (T_c/T_{c,max})$ for various organs of species, where subscript max represents the entire stem-crown system, as shown in FIG. 27.

|  |  | Eq. (44) | | | | Eq. (45) | | | | | |
| --- | --- | --- | --- | --- | --- | --- | --- | --- | --- | --- | --- |
|  | Species (N) | A | $R^2$ | B | $R^2$ | A | $R^2$ | B | $R^2$ | $k_{reg}$ | $R^2$ |
| Full trees | Pig RCA (11) | 1 | 1 | 1 | 1 | 1.000 | 1 | 1.000 | 1 | 6.5E−05 | 1.000 |
|  | Pig LAD (11) | 1 | 1 | 1 | 1 | 1.000 | 1 | 1.000 | 1 | 7.0E−05 | 1.000 |
|  | Pig LCx (10) | 1 | 1 | 1 | 1 | 1.000 | 1 | 0.999 | 1 | 5.7E−05 | 1.000 |
|  | Rat PA (11) | 1 | 1 | 1 | 1 | 1.000 | 1 | 0.999 | 1 | 2.2E−02 | 1.000 |
|  | Cat PA (10) | 1 | 1 | 1 | 1 | 1.000 | 1 | 0.999 | 1 | 1.3E−02 | 1.000 |
|  | Cat PV (10) | 1 | 1 | 1 | 1 | 1.000 | 1 | 0.999 | 1 | 5.3E−02 | 1.000 |
|  | Human PA (17) | 1 | 1 | 1 | 1 | 1.000 | 1 | 1.000 | 1 | 1.0E−03 | 1.000 |
|  | Human PA (15) | 1 | 1 | 1 | 1 | 1.000 | 1 | 1.000 | 1 | 4.7E−03 | 1.000 |
|  | Human PA (17) | 1 | 1 | 1 | 1 | 1.000 | 1 | 0.992 | 1 | 1.1E−03 | 1.000 |
|  | Human PV (15) | 1 | 1 | 1 | 1 | 1.000 | 1 | 1.000 | 1 | 4.2E−02 | 1.000 |
|  | Human PV (15) | 1 | 1 | 1 | 1 | 1.000 | 1 | 1.000 | 1 | 3.6E−04 | 1.000 |
|  | Rat MA (4) | 1 | 1 | 1 | 1 | 1.003 | 1 | 0.959 | 1 | 9.2E−05 | 1.000 |
|  | Rabbit OV (4) | 1 | 1 | 1 | 1 | 1.017 | 0.994 | 0.873 | 1 | 1.1E−03 | 0.994 |
|  | Human BCA (5) | 1 | 1 | 1 | 1 | 1.004 | 1 | 0.973 | 1 | 3.1E−07 | 1.000 |
|  | Human BCV (5) | 1 | 1 | 1 | 1 | 1.002 | 1 | 0.966 | 1 | 4.7E−06 | 1.000 |
|  | Hamster RMA (4) | 1 | 1 | 1 | 1 | 1.002 | 0.987 | 0.955 | 1 | 9.9E−05 | 1.000 |
|  | Cat SMA (4) | 1 | 1 | 1 | 1 | 1.005 | 0.999 | 0.951 | 1 | 3.6E−05 | 0.999 |
| Proximal trees | Pig RCA (2) | 1 | 1 | 1 | 1 | 1.000 | 1 | 0.899 | 1 |  |  |
|  | Pig LAD (2) | 1 | 1 | 1 | 1 | 1.001 | 0.999 | 0.906 | 1 |  |  |
|  | Human PA (6) | 1 | 1 | 1 | 1 | 1.000 | 1 | 0.998 | 1 |  |  |
|  | Human PA (7) | 1 | 1 | 1 | 1 | 1.000 | 1 | 0.997 | 1 |  |  |
|  | Mean ± SD | 1 |  | 1 |  | 1.002 ± 0.004 |  | 0.974 ± 0.037 |  |  |  |

The proportionality constant (k) in Eq. #45 was obtained from linear regression in various vascular trees; $R^2$ is correlation coefficient; N stands for the number of vessel generations in the respective tree. RCA, right coronary artery; LAD, left anterior descending artery; LCx, left circumflex artery; PA, pulmonary artery; PV, pulmonary vein; SMA, sartorius muscle arteries; MA, mesentery arteries; OV, omentum veins; BCA, bulbular conjunctiva arteries; RMA, retractor muscle artery. For details of analyses and anatomical data see Examples and Validation provided below.

Physiological and Clinical Implications

The transit time of blood through a vascular system is a seminal physiological parameter that dictates biological transport phenomena and has critical implications for vascular disease. For example, the MTT is a valuable indicator of cerebral circulation. Additionally, perfusion pressure responds to even slight changes in the MTT and ischemia and hemodynamic impairment are also associated with the MTT. Furthermore, in at least one exemplary application of the present disclosure, the novel analytical relationships for MTT disclosed herein (Equations #44 and #45) provide a theoretical basis for understanding the pharmacokinetic processes that govern tissue distribution of oxygen and nutrients under physiological conditions, as well as drug permeation and diffusion in pathological conditions. The pharmacokinetics of drugs plays a significant role in determining the pharmacological effect thereof. As drugs are often carried in the blood through the vasculature to reach a targeted tissue (e.g., to target a tumor cells), the precise prediction of transit time can have extremely important implications for the efficacy of drug dosing. Accordingly, the MTT plays a vital role in pharmacokinetics and drug distribution.

Conventional measurement of the MTT requires accurate quantification of blood volume and flow rate, both of which are challenging to accurately determine, particularly in small vessels. Although non-invasive imaging techniques such as phase-contrast MRI and Doppler ultrasound have been shown to quantify flow rate in blood vessels, analytical relations for calculation of the MTT in complex vascular trees obviate the need for flow measurement. Since the novel scaling laws for MTT herein are functions of morphological parameters of vascular trees (e.g., diameter and length of blood vessels), the scaling laws along with non-invasive imaging techniques can be used for measurement of MTT. For example, in at least one embodiment, the non-invasive imaging techniques set forth in U.S. patent application Ser. No. 12/505,685 to Kassab et al., which is hereby incorporated by reference herein in its entirety, may be utilized in determining morphological parameters of the desired vascular trees. Despite this specific example, it will be appreciated that any appropriate techniques may be utilized to provide the necessary vascular parameters.

The validated scaling laws disclosed herein not only provide a theoretical basis for fundamental studies of drug distribution in various organs, but also may have clinical diagnostic implications since they not only hold true for the full trees (i.e. down to the pre-capillary level), but also for proximal trees (i.e. down to about 1 mm diameter vessels which can be observed in angiograms). Because of this, standard clinical imaging of blood vessel anatomy can be used in conjunction with the novel scaling laws hereof to yield functional data on the transit times through an organ or other vasculature of interest.

Examples and Validation

Materials and Methods

Based on conventionally available morphometric data of vascular trees in various organs and species, the transit time scaling laws were quantitatively assessed. As the capillary network is not a tree-like structure, it was excluded from the analysis. Instead, the analysis considered a formulation for tree structures of various species and organs from most distal vessel to pre-capillary vessels. The following morphometric databases were used to validate the novel scaling law formulations hereof for transit time: coronary arterial tress of pig hearts by G. S. Kassab, C. A. Rider, N. J. Tang, Y. C. Fung, *Morphometry of pig coronary arterial trees*, Am J Appl Physiol 265: H350-65 (1993); pulmonary arterial tree of rats from the study of Z. L. Jiang, G. S. Kassab, Y. C. Fung, *Diameter-defined Strahler system and connectivity matrix of the pulmonary arterial tree*, J Appl Physiol (1985) 76: 882-92 (1993); pulmonary arterial/venous trees of cats from R. T. Yen et al., *Morphometry of cat pulmonary venous tree*, J Appl Physiol: Respiratory, Environmental, and Exercise Physiology 55: 236-42 (1983) and R. T. Yen et al., *Morphometry of cat pulmonary venous tree*, J of Biomech Eng; pulmonary arterial trees of humans from S. Singhal, R. Henderson, K. Horsfield, K. Harding, G. Cumming, *Morphometry of the human pulmonary arterial tree*, Circ Res 33: 190-97 (1973), S. S. Singhal, G. Cumming, K. Horsfield, L. K. Harking, *Morphometric study of pulmonary arterial tree and haemodynamics*. J Assoc Physicians India 21: 719-22 (1973), and W. Huang, R. Yen, M. McLaurine, G. Bledsoe, *Morphometry of the human pulmonary vasculature*, J Appl Physiol 81: 2123-133 (1996); pulmonary venous trees of humans from K. Horsfield and W. I. Gordon, *Morphometry of pulmonary veins in man*, Lung 159: 211-18 (1981) and W. Huang, R. Yen, M. McLaurine, G. Bledsoe, *Morphometry of the human pulmonary vasculature*, J Appl Physiol 81: 2123-133 (1996); retractor muscle arterial tree of hamsters from M. L. Ellsworth, A. Liu, B. Dawant, A. S. Popel, R. N. Pittman, *Analysis of vascular pattern and dimensions in arteriolar networks of the retractor muscle in young hamsters*, Microvascular Res 34: 168-83 (1987); mesentery arterial tree of rats from K. Key, A. R. Pries, P. Gaehtgens, *Topological structure of rat mesenteric microvessel networks*, Microvascular Res 32: 315-332 (1986); sartorius muscle arterial tree of cats from A. Koller, B. Dawant, A. Liu, A. S. Popel, P. C. Johnson, *Quantitative analysis of arteriolar network architecture in cat Sartorius muscle*, Am J Physiol 253: H154-64 (1987); and bulbular conjunctiva arterial/venous trees of humans and the omentum arterial tree of rabbits from B. M. Fenton and B. Zweifach, *Microcirculatory model relating to geometrical variation to changes in pressure and flow rate*, Annals of Biomed Eng 9, 303-21 (1981).

Data Analysis

A power law relation was used to validate the novel scaling law relations hereof. The scaling law has a general form as follows:

$$Y = A'X^B \quad (E.1)$$

For the validation of Equation (44), X and Y were defined as $(T_s/T_c)$ and $(V_s/V_c)$, respectively. The theoretical values of A and B should be equal to one. A nonlinear regression was used to obtain the power law exponent, with A constrained to 1 (i.e., $Y=X^B$); parameter A was also obtained with B constrained to 1 (i.e., $=A'X$). To test Equation (45), normalized X and Y were defined as $(T_c/T_{c,max} \times L_c/L_{c,max})$ and $(V_c/V_{c,max})$, respectively. Similarly, parameter A and B were obtained as listed in Table 1; the theoretical values of A and B should be equal to one. To estimate the proportionality constant (k) in Equation (45): $V_c = k(T_c \times L_c)$, X and Y were defined as $(T_c \times L_c)$ and $(V_c)$, respectively, the parameter k was also estimated using linear model $(Y=A'X)$.

Derivation of Analytical Relations

The volumetric flow rate is defined as:

$$Q = \lim_{\Delta t \to 0} \frac{\Delta V}{\Delta t} = \frac{dV}{dt} \quad (E.2)$$

Using Equation E.2, the volume that is transported within the network between $t=t_0$ and $t=t_0+T$ can be obtained as:

$$V = \int_{t=t_0}^{t=t_0+T} Q\,dt \quad (E.3)$$

where $t_0$ is initial time and T is interval. The time-averaged flow rate from $t=t_0$ and $t=t_0+T$ is expressed as:

$$\overline{Q} = \frac{\int_{t=t_0}^{t=t_0+T} Q\,dt}{T} \quad (E.4)$$

Based on the assumption that particles travel with blood velocity and blood is an incompressible fluid, the amount of blood volume that leaves the segment during mean transit time of the segment ($T_s$) is equal to the segment volume. As such, the volume of vessel segment can be obtained as:

$$V_s = \int_{t=t_0}^{t=t_0+T_s} Q_s\,dt = \overline{Q}_s \times T_s \quad (E.5)$$

where $\overline{Q}_s$ is time-averaged flow rate during $T_s$ mean transit time. Similarly, the volume of the crown (i.e. intravascular volume of the network) can be expressed as:

$$V_c = \int_{t=t_0}^{t=t_0+T_c} Q_c\,dt = \overline{Q}_c \times T_c \quad (E.6)$$

where $T_c$ and $\overline{Q}_s$ are mean transit time of crown and time-averaged flow rate during $T_c$, respectively. The volume of the crown is also equivalent to the sum of all vessel segments in the network as follows:

$$V_c = \sum_{i=1}^{n} (V_s)_i = \sum_{i=1}^{n} (\overline{Q}_s \times T_s)_i \quad (E.7)$$

where n is the total number of vessels in the networks and i=1 represents the most proximal segment (stem). Accordingly, using Equations (E.5), (E.6), and (E.7), the flow rate of the crown can be written as:

$$\overline{Q}_c = \frac{\sum_{i=1}^{n} \overline{Q}_{s,i} \times T_i}{T_c} \quad (E.8)$$

The flow fraction (FF) is defined as the ratio of flow rate of a vessel segment to the flow rate of the stem as:

$$FF_i = \frac{Q_{s,i}}{Q_{s,1}} \quad (E.9)$$

In general, FF is a positive number (FF≥0). Using this definition, Equation (E.8) can be rewritten as:

$$\overline{Q}_c = \left(\frac{\sum_{i=1}^{n} (FF)_i \times T_i}{T_c}\right) \overline{Q}_{s,1} \quad (E.10)$$

As discussed herein, the particles take various paths to travel through a network. Accordingly, the mean transit time in the entire network is equal to the weighted average of the time the particles require to travel through the network. Assuming that the total number of particles travelling through a segment during $T_s$ is proportional to time-averaged flow rate of the segment over $T_s$, the mean transit time in the crown can be obtained as:

$$T_c = \sum_{i=1}^{n} (FF)_i \times T_{s,i} \quad (E.11)$$

The validity of this Equation (E.11) can be easily justified for a network of vessels in series (FF=1), or an idealized symmetrical network of vessels. Using Equations (E.10) and (E.11), the conclusion can be reached that the time-averaged flow rate over $T_c$ in the crown is equal to the time-averaged flow rate of the stem over $T_s$ ($\overline{Q}_c = \overline{Q}_{s,1}$). From elimination of Q between Equation (E.6) and Equation (E.5), the relationship between the ratio of vessel segment transit time to crown transit time and segment volume to the crown volume can be obtained as:

$$\frac{T_s}{T_c} = \frac{V_s}{V_c} \quad (E.12)$$

While various embodiments of systems and methods to determine optimal diameters of vessel segments in a bifurcation have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments of the present disclosure, the specification may have presented the method and/or process of the present disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present disclosure should not be limited to the performance of their steps in the order written, and one skilled in the art can readily appreciate that the sequences may be varied and still remain within the spirit and scope of the present disclosure.

The invention claimed is:

1. A method for designing microfluidic channels, the method comprising the steps of:
   using a processor to produce a microfluidic tree image showing at least part of a microfluidic tree comprising at least a microfluidic channel segment, wherein the processor is operably connected to a storage medium capable of receiving and storing the image;
   determining a transit time in the microfluidic channel segment;

determining a volume in the microfluidic channel segment;

determining a volume in a first microfluidic tree comprising the microfluidic channel segment; and calculating a transit time in the first microfluidic tree based upon information from the microfluidic tree image and the transit time through the microfluidic channel segment, the volume in the microfluidic channel segment, and the volume in the first microfluidic tree;

wherein a first ratio of the transit time in the microfluidic channel segment and the transit time in the first microfluidic tree and a second ratio of the volume in the microfluidic channel segment and the volume in the first microfluidic tree have a linear relationship; and wherein comparing the first ratio with the second ratio results in a proportionality constant that is equal to about 1.

2. The method of claim 1, further comprising the step of calculating a constant based on a length of the first microfluidic tree, the volume of the first microfluidic tree, and the calculated transit time in the first microfluidic tree.

3. The method of claim 2, further comprising the steps of:
determining a length and a volume of a second microfluidic tree; and
calculating a transit time in the second microfluidic tree based upon the use of the calculated constant.

4. The method of claim 1, wherein the transit time in the first microfluidic tree is calculated without measuring flow rates.

5. A method for optimizing the dosage of a pharmaceutical compound comprising at least one active ingredient, the method comprising the steps of:
using a processor to produce a biological tree image from a mammalian body showing a vasculature of at least part of a biological tree comprising at least a vessel segment, wherein the processor is operably connected to a storage medium capable of receiving and storing the image;
determining a transit time in the vessel segment;
determining a blood volume in the vessel segment;
determining a blood volume in a first vascular tree comprising the vessel segment;
calculating a transit time in the first vascular tree based upon information from the biological tree image and the transit time through the vessel segment, the blood volume in the vessel segment, and the blood volume in the first vascular tree; and
modifying a composition of a pharmaceutical compound comprising at least one active ingredient based on the calculated transit time and a location of a targeted tissue within the mammalian body.

6. The method of claim 5, further comprising the steps of:
calculating a constant based on a length of the first vascular tree, the volume of the first vascular tree, and the calculated transit time in the first vascular tree; and
using the constant to calculate a second transit time within a second vasculature tree at the targeted tissue;
wherein the step of modifying the composition of a pharmaceutical compound is further performed based on the calculated second transit time.

7. The method of claim 5, wherein a first ratio of the transit time in the vessel segment and the transit time in the first vascular tree and a second ratio of the blood volume in the vessel segment and the volume in the first vascular tree have a linear relationship.

8. The method of claim 7, wherein comparing the first ratio with the second ratio results in a proportionality constant that is equal to about 1.

9. The method of claim 5, further comprising the step of calculating a constant based on a length of the first vascular tree, the volume of the first vascular tree, and the calculated transit time in the first vascular tree.

10. The method of claim 9, further comprising the steps of:
determining a length and a blood volume of a second vascular tree; and
calculating a transit time in the second vascular tree based upon the use of the calculated constant.

11. The method of claim 5, wherein the step of using the processor to produce the biological tree image is performed using a non-invasive imaging technique.

12. A method for diagnosing disease in a mammalian biological tree, the method comprising the steps of:
obtaining a baseline transit time for a model mammalian vascular tree;
using a processor to produce a biological tree image from a mammalian body showing a vasculature of at least part of a biological tree comprising at least a vessel segment, wherein the processor is operably connected to a storage medium capable of receiving and storing the image;
determining a transit time in the vessel segment;
determining a blood volume in the vessel segment;
determining a blood volume in a first vascular tree comprising the vessel segment;
calculating a first transit time in the first vascular tree based upon information from the biological tree image and the transit time through the vessel segment, the blood volume in the vessel segment, and the blood volume in the first vascular tree; and
comparing the baseline transit time with the first transit time in the first vascular tree to determine the extent of vessel and/or organ disease;
wherein the comparison of the baseline transit time and the first transit time indicates an inefficiency of 10% or higher;
wherein the model mammalian vascular tree is physiologically comparable to the mammalian vascular tree.

13. The method of claim 12, further comprising the steps of:
calculating a constant based on a length of the first vascular tree, the volume of the first vascular tree, and the calculated transit time in the first vascular tree;
determining a length and a volume of a second vascular tree;
calculating a second transit time in the second vascular tree based upon the use of the calculated constant; and
comparing the first transit time of the first vascular tree with the second transit time of the second vascular tree to determine the extent of vessel and/or organ disease.

14. The method of claim 12, wherein a first ratio of the transit time in the vessel segment and the transit time in the first vascular tree and a second ratio of the blood volume in the vessel segment and the blood volume in the first vascular tree have a linear relationship.

15. The method of claim 12, wherein the transit time in the first vascular tree is calculated without measuring blood flow rates.

16. The method of claim 12, wherein the step of using the processor to produce the biological tree image is performed using a non-invasive imaging technique.

* * * * *